United States Patent

Matsuo et al.

Patent Number: 4,725,591
Date of Patent: Feb. 16, 1988

[54] β-LACTAMASE INHIBITORY COMPOSITION

[75] Inventors: Taisuke Matsuo, Ibaraki; Mitsuzo Kuno, Takatsuki; Kenji Okonogi, Mishima, all of Japan

[73] Assignee: Takeda Chemical Industries, Ltd., Osaka, Japan

[21] Appl. No.: 576,776

[22] Filed: Feb. 3, 1984

Related U.S. Application Data

[62] Division of Ser. No. 314,512, Oct. 23, 1981, abandoned.

[30] Foreign Application Priority Data

Oct. 23, 1980 [WO] PCT Int'l Appl. ... PCT/JP80/00255
Dec. 4, 1980 [WO] PCT Int'l Appl. ... PCT/JP80/00295

[51] Int. Cl.$^4$ .................. A61K 31/545; A61K 31/395; A61K 31/535
[52] U.S. Cl. ..................... 514/200; 514/210; 514/435
[58] Field of Search ............... 424/114, 117; 514/183, 514/149, 200, 210, 435

[56] References Cited

U.S. PATENT DOCUMENTS 4,225,586  9/1980  Imada et al. .................. 424/117
4,229,436  10/1980  Imada et al. .................. 424/117

FOREIGN PATENT DOCUMENTS 0021678  1/1981  European Pat. Off. .
2071650  9/1981  United Kingdom ........... 260/239 A

OTHER PUBLICATIONS

Shibuya et al., *Heterocycles*, vol. 12, No. 10, 1979, pp. 1315–1318.
Sykes et al., *Nature*, vol. 291, pp. 489–491 (1981).
Aoki et al., *The Japanese Journal of Antibiotics*, vol. XXX Supl., pp. S-207-S-217 (1977).
Reading et al., *Antimicrobial Agents and Chemotherapy*, vol. 11, No. 5, May 1977, pp. 852–857.
Matsuo et al., *Chem. Abs.* 97, 162701j (1982).

Primary Examiner—J. R. Brown
Assistant Examiner—John W. Rollins, Jr.
Attorney, Agent, or Firm—Wenderoth, Lind & Ponack

[57] ABSTRACT

Compounds having one or two substituents at the 3-position, represented by the general formula

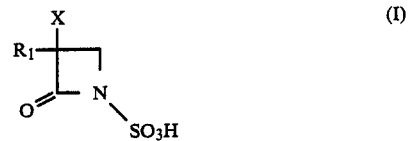

wherein $R_1$ is an optionally acylated or protected amino group and X is hydrogen atom or methoxy group, or a pharmaceutically acceptable salt thereof; when used either alone or in combination with a β-lactam antibiotic, show excellent β-lactamase inhibitory activity and can be used as drugs for use in humans and domestic animals.

9 Claims, No Drawings

β-LACTAMASE INHIBITORY COMPOSITION

This application is a division of application Ser. No. 314,512, filed Oct. 23, 1981 (now abandoned).

This invention relates to a novel β-lactamase inhibitor consisting of a 1-sulfo-2-oxoazetidine compound and to a novel antimicrobial composition containing the inhibitor.

Recent researches in semisynthetic antibiotics have made an important contribution to treatment of infectious diseases. On the other hand, development of resistant bacterial strains to these semisynthetic antibiotics is one of the most important problems. It has recently been proposed that a β-lactamase inhibitor is used against β-lactamase-producing resistant bacterial strains. In fact, such a novel β-lactamase inhibitor as clavulanic acid [Antimicrobial Agents and Chemotherapy, 11, 852 (1977)] has been found, but its β-lactamase inhibitory activity is unsatisfactory or even ineffective against some bacteria.

The present invention relates to a β-lactamase inhibitory composition containing a compound represented by the formula

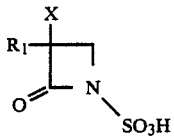
(I)

wherein $R_1$ is an optionally acylated or protected amino group and X is hydrogen atom or methoxy group, or a pharmaceutically acceptable salt thereof and such a β-lactamase inhibitory composition containing said compound in combination with a β-lactam antibiotic.

The present inventors have found that 1-sulfo-2-oxoazetidine derivatives of general formula (I) have excellent β-lactamase inhibitory activity, and, as a result of continued research, have now completed the present invention.

Thus, the present invention is concerned with a β-lactamase inhibitory composition containing compound of the general formula [I], wherein $R_1$ and X have the same meanings as defined above and a β-lactamase inhibitory composition also contains a β-lactam antibiotic.

In the above general formula, when $R_1$ is an acylated amino, the acyl group on said amino group includes those acyl groups that are substituents on the amino group at position 6 of so far known penicillin derivatives or on the amino group at position 7 of konwn cephalosporin derivatives.

Such acyl group includes among others (1) a group represented by the formula

$R_6$—CO— wherein $R_6$ is a lower alkyl, optionally substituted phenyl, heterocyclic group, or optionally substituted benzoyl group;

(2) a group represented by the formula

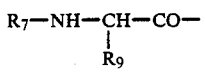

wherein $R_7$ is hydrogen atom, an optionally substituted amino acid residue, an amino-protecting group or a group represented by the formula $R_8$—$(CH_2)_{n1}$—CO— wherein $R_8$ is an optionally substituted heterocyclic group, optionally substituted phenyl, optionally substituted lower alkyl, optionally substitued phenylthio, or lower alkylthio, and $n_1$ is 0 or an integer of 1–4, and the —$(CH_2)_{n1}$-group may be substitued, or the formula $(R_8')(R_8'')$N—CO— in which $R_8'$ and $R_8''$ are the same or different and each is hydrogen atom or a lower alkyl, lower alkylcarbamoyl, optionally substituted phenylcarbonyl, or sulfo group, or the formula $R_8'''$—$SO_2$— wherein $R_8'''$ is an optionally substituted lower alkyl group, and $R_9$ is hydrogen atom or an optionally substituted lower alkyl, optionally substituted phenyl, optionally substituted heterocyclic group, cycloalkenyl, or optionally substituted heterocycle-carbonylamino group, said heterocycle-carbonylamino group optionally containing an intermediary alkylene chain;

(3) a group represented by the formula

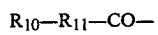
$R_{10}$—$R_{11}$—CO— wherein $R_{10}$ is a group represented by the formula

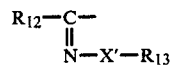

wherein X' is oxygen or sulfur atom, $R_{12}$ is an optionally substituted heterocyclic group or optionally substituted phenyl group, and $R_{13}$ is hydrogen atom, an optionally substituted phenyl, lower acyl, or lower alkyl group, or a group of the formula —$R_{14}$—$R_{15}$ ($R_{14}$ being lower alkylene or lower alkenylene and $R_{15}$ being carboxyl, esterified carboxyl or heterocyclic group), and $R_{11}$ is a mere single bond or a group represented by the formula

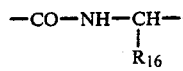

wherein $R_{16}$ is a lower alkyl, optionally substituted phenyl, or optionallly substituted heterocyclic group;

(4) a group represented by the formula

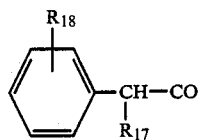

wherein $R_{17}$ is hydroxyl, hydroxysulfonyloxy, carboxyl, an optionally substituted sulfamoyl, sulfo, an optionally substituted phenoxycarbonyl, benzyloxycarbonyl, formyloxy, phthalimido, azido or halogen and $R_{18}$ is hydrogen atom or a lower alkyl, lower alkoxy, halogen, azido, nitro or hydroxyl group; and (5) a group represented by the formula

$R_{19}$—$R_{20}$—$CH_2$—CO— wherein $R_{19}$ is cyano, optionally substituted phenyl, optionally substituted phenoxy, optionally substituted lower alkyl, optionally substituted alkenylene or optionally substituted heterocyclic group, and $R_{20}$ is a mere single bond or —S—.

In the above formula, the lower alkyl group represented by $R_6$ preferably contains 1-6 carbon atoms. The heterocyclic moiety of the optionally substituted heterocyclic group includes 5- or 6-membered heterocyclic groups containing one or two nitrogen atoms with or without one oxygen atom. Concrete examples of said heterocyclic group are isoxazolyl, piperazinyl and imidazolinyl. The substituent on said heterocyclic group includes among others $C_{1-3}$ lower alkyl, $C_{1-3}$ lower alkoxy, halogen, nitro, amino, oxo, thioxo and optionally substituted phenyl. The substituent on said optionally substituted phenyl includes among others $C_{1-3}$ lower alkyl, $C_{1-3}$ lower alkoxy, halogen, nitro and amino.

Referring to the optionally substituted amino acid residue represented by $R_7$ in the above formula includes among others glycyl, alanyl, valyl, leucyl, isoleucyl, seryl, threonyl, cysteinyl, cystyl, methionyl, $\alpha$- or $\beta$-aspartyl, $\alpha$- or $\gamma$-glutamyl, lysyl, arginyl, phenylalanyl, phenylglycyl, tyrosyl, histidyl, tryptophyl and prolyl. The substituent on said optionally substituted amino acid residues includes among others amino, lower alkylamino, amino-protecting groups, carbamoyl, methylcarbamoyl, sulfamoyl, benzyl, 4-ethyl-2,3-dioxo-1-piperazinecarbonyl, and 4-ethyl-2,3-dioxo-1-piperazinecarbonylamino. The lower alkyl in said lower alkylamino preferably contains 1-3 carbon atoms. Said amino-protecting group includes those mentioned as examples of the amino-protecting group mentioned hereinafter.

The amino-protecting group represented by $R_7$ includes those mentioned as examples of the amino-protecting group mentioned hereinafter.

The heterocyclic moiety of the optionally substituted heterocyclic group represented by $R_8$ in the formula $R_8-(CH_2)_{n1}-CO-$, includes among others 5- or 6-membered heterocyclic groups containing one sulfur, nitrogen or oxygen atom, 5- or 6-membered heterocyclic groups containing 2-4 nitrogen atoms, and 5- or 6-membered heterocyclic groups containing one or two nitrogen atoms and one sulfur or oxygen atom. These heterocyclic groups may be condensed with a 6-membered ring containing not more than two nitrogen atoms, a benzene ring, or a 5-membered ring containing one sulfur atom.

Concrete examples of the heterocyclic group represented by the above $R_8$ are 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthyridinyl, 1,5-naphthyridinyl, 1,6-naphthyridinyl, 1,7-naphthyridinyl, 2,7-naphthyridinyl, 2,6-naphthyridinyl, quinolyl, thieno[2,3-b]pyridinyl, tetrazolyl, thiadiazolyl, oxadiazolyl, triazinyl, thienyl, pyrrolyl and furyl.

The substituent on the optionally substituted heterocyclic group represented by $R_8$ includes among others optionally substituted $C_{1-12}$ alkyl, $C_{1-3}$ lower alkoxy, hydroxyl, oxo, thioxo, formyl, trifluoromethyl, amino, halogen, $C_{1-3}$ lower alkylsulfonyl, 2,6-dichlorophenyl, coumarin-3-carbonyl, 4-formyl-1-piperazinyl, pyrrolaldimino, furanaldimino, thiophenealdimino, mesyl, amino-protecting groups, and optionally halo-substituted $C_{2-4}$ acylamino. Said amino-protecting groups include those mentioned as examples of the later-mentioned amino-protecting group. The optional substituent on the $C_{1-12}$ alkyl includes among other phenyl, halogen, hydroxyl and dialkylamino. The alkyl moiety of said dialkylamino is preferably a lower one of 1-3 carbon atoms.

The substituent on the optionally substituted phenyl represented by $R_8$ includes among others $C_{1-3}$ lower alkyl, $C_{1-3}$ lower alkoxy, halogen, hydroxyl and amino.

Referring to the lower alkylthio represented by $R_8$, the lower alkyl preferably contains 1-3 carbon atoms.

The substituent on the optionally substituted phenylthio represented by $R_8$ includes among others $C_{1-3}$ lower alkyl, $C_{1-3}$ lower alkoxy, halogen, hydroxyl and amino.

The optional substituent on the group represented by the formula $-(CH_2)_{n1}-$ includes among others amino and groups represented by the formula $-NH-CO-R_8''''$ wherein $R_8''''$ is amino or optionally substituted piperazinyl. The substituent on said optionally substituted piperazinyl represented by $R''''$ includes among others $C_{1-3}$ lower alkyl, $C_{1-3}$ lower alkoxy, hydroxyl, oxo, thioxo and halogen.

The lower alkyl represented by $R_8'$ and/or $R_8''$ in the above formula preferably contains 1-3 carbon atoms. The lower alkyl moiety in the lower alkylcarbamoyl preferably contains 1-3 carbom atoms. The substituent on the optionally substituted phenylcarbonyl includes among others $C_{1-3}$ lower alkyl, $C_{1-3}$ lower alkoxy, halogen, hydroxyl, hydroxysulfonyloxy and benzyloxy.

The lower alkyl moiety of the optionally substituted lower alkyl represented by $R_8'''$ in the formula $R_8'''-SO_2-$ preferably contains 1-6 carbon atoms, and the substituent, which may be found in one or two positions, includes among others amino, carboxyl, benzyloxycarbonyl and protected amino group. The protective group in said protected amino includes those mentioned as examples of the amino-protecting group mentioned hereinafter.

The lower alkyl moiety of the optionally substituted lower alkyl group represented by $R_9$ preferably contains 1-3 carbon atoms. The substituent thereon includes among others phenyl, carbamoyl, methylcarbamoyl, methylthio, thienylacetamido, ethoxycarbonylmethylcarbamoyl, N-methyltetrazolylthio, halogen and sulfamoyl.

Referring to the optionally substituted phenyl represented by $R_9$, the substituent thereon includes among others $C_{1-3}$ lower alkyl, $C_{1-3}$ lower alkoxy, halogen, hydroxyl, hydroxysulfonyloxy, benzyloxy, benzoyloxy, trimethylsilyl and $C_{2-10}$ acyloxy.

The heterocyclic moiety of the optionally substituted heterocyclic group represented by $R_9$ includes among others 5-membered heterocyclic groups containing one sulfur, nitrogen or oxygen atom, 5-membered heterocyclic groups containing one or two nitrogen atoms and one sulfur or oxygen atom, and 5- or 6-membered heterocyclic groups containing 2-4 nitrogen atoms. Concrete examples of said heterocyclic groups are thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl and oxadiazolyl. The optional substituent thereon includes among others $C_{1-3}$ lower alkyl, $C_{1-3}$ lower alkoxy, halogen, hydroxyl, nitro, hydroxysulfonyloxy, amino and optionally halo-substituted $C_{2-4}$ acylamino.

The cycloalkenyl represented by $R_9$ is preferably 5- or 6-membered, for example, cyclohexenyl or cyclohexadienyl.

The heterocyclic moiety of the optionally substituted heterocycle-carbonylamino group, which may contain an intermediary alkylene chain, represented by $R_9$ includes 6-membered heterocyclic groups containing two nitrogen atoms, such as piperazinyl. The substituent thereon includes among others $C_{1-12}$ alkyl, $C_{1-3}$ lower alkoxy, oxo, thioxo and amino. Said alkylene chain is preferably of 1-3 carbon atoms, for example methylene, ethylene or n-propylene.

The heterocyclic moiety of the optionally substituted heterocyclic group $R_{12}$ in the group $R_{10}$ which is represented by the formula

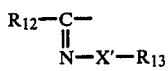

includes 5-membered heterocyclic groups containing one nitrogen, sulfur or oxygen atom with or without one nitrogen atom. Concrete examples of the heterocyclic group are 2-thiazolyl, 4-thiazolyl, 5-thiazolyl, 2-thienyl, 3-thienyl, 2-furyl, 3-furyl, 2-pyrrolyl and 3-pyrrolyl. The heterocyclic group may be substituted by such a substituent as $C_{1-3}$ lower alkyl, $C_{1-3}$ lower alkoxy, hydroxyl, mesyl, halogen, imino, amino, mesylamino or optionally halo-substituted $C_{2-4}$ acylamino.

Referring to the optionally substituted phenyl represented by $R_{12}$, the substituent thereon includes among others $C_{1-3}$ lower alkyl, $C_{1-3}$ lower alkoxy, halogen, nitro, amino, hydroxyl or substituted hydroxyl. The substituent of said substituted hydroxyl includes among others benzyl, benzoyl, $C_{2-10}$ acyl, $\gamma$-D-glutamyl and 3-amino-3-carboxypropyl.

The lower alkyl represented by $R_{13}$ preferably contains 1-3 carbon atoms.

Referring to the optionally substituted phenyl represented by $R_{13}$, the substituent thereon includes among others lower alkyl, lower alkoxy and halogen.

The lower acyl moiety of the optionally substituted lower acyl represented by $R_{13}$ preferably contains 2-4 carbon atoms, and the substituent thereon is, for example, a halogen atom.

The lower alkenylene $R_{14}$ in the formula $-R_{14}-R_{15}$ (i.e. $R_{13}$) preferably contains 1-3 carbon atoms, and examples thereof are methylene, dimethylmethylene, ethylene and methylethylene.

The lower alkenylene represented by $R_{14}$ preferably contains 2-3 carbon atoms, and examples thereof are vinylene and propenylene.

The carboxylate ester group represented by $R_{15}$ includes among others the methyl, ethyl and propyl esters.

The heterocyclic group represented by $R_{15}$ includes 6-membered heterocyclic groups containing one nitrogen atom and one oxygen atom. Morpholino is an example.

The lower alkyl $R_{16}$ in the formula

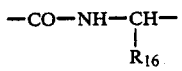

or $R_{11}$ preferably contains 1-3 carbon atoms.

Referring to the optionally substituted phenyl represented by $R_{16}$, the substituent thereon includes among others $C_{1-3}$ lower alkyl, $C_{1-3}$ lower alkoxy, halogen, nitro, amino and $C_{2-10}$ acyloxy.

The optionally substituted heterocyclic group represented by $R_{16}$ includes among others 5-membered heterocyclic groups one sulfur, nitrogen or oxygen atom, 5-membered heterocyclic groups containing one or two nitrogen atoms and one sulfur or oxygen atom, and 5-membered heterocyclic groups containing 2-4 nitrogen atoms. Concrete examples of said heterocyclic groups are thiazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl. The substituent thereon includes among others $C_{1-3}$ lower alkyl, $C_{1-3}$ lower alkoxy, halogen, hydroxyl, amino, and optionally halo-substituted $C_{2-4}$ acylamino.

Referring to the optionally substituted sulfamoyl represented by $R_{17}$, the substituent thereon includes among others $C_{1-3}$ lower alkyl and amidino.

Referring to the optionally substituted phenoxycarbonyl represented by $R_{17}$, the substituent thereon includes $C_{1-3}$ lower alkyl and $C_{1-3}$ lower alkoxy.

The lower alkyl or lower alkoxy represented by $R_{18}$ preferably contains 1-3 carbon atoms.

Referring to the optionally substituted phenyl $R_{19}$ in the above-mentioned formula, the substituent thereon includes among others $C_{1-3}$ lower alkyl, $C_{1-3}$ lower alkoxy, halogen, nitro, amino, hydroxyl and substituted aminomethyl. The substituent on said substituted aminomethyl is, for example, carbamoyl, (2-oxo-3-benzylideneaminoimidazolidin-1-yl)carbonyl or (2-oxoimidazolidin-1-yl)carbonyl.

Referring to the optionally substituted phenoxy represented by $R_{19}$, the substituent thereon includes among others $C_{1-3}$ lower alkyl, $C_{1-3}$ lower alkoxy, halogen, nitro amino, hydroxyl and aminomethyl, as in the case of the substituent on the above-mentioned phenyl group represented by $R_{19}$. Referring to the optionally substituted lower alkyl represented by $R_{19}$, the lower alkyl is preferably of 1-6 carbon atoms, and the substituent thereon is, for example, halogen, hydroxyl, cyano or trifluoromethyl.

The alkenylene moiety of the optionally substituted alkenylene represented by $R_{19}$ is, for example, vinylene or propenylene, and the substituent thereon is, for example, carboxyl or cyano.

The heterocyclic moiety of the optionally substituted heterocyclic group represented by $R_{19}$ includes 5- or 6-membered heterocyclic groups containing one sulfur atom or one to four nitrogen atoms and 5- or 6-membered heterocyclic groups containing one sulfur atom and one nitrogen or oxygen atom. Concrete examples of the heterocyclic group are 2-thineyl, benzothienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiinyl.

Referring to the optionally substituted heterocyclic group represented by $R_{19}$, the substituent thereon includes among others $C_{1-3}$ lower alkyl, $C_{1-3}$ lower alkoxy, halgoen, nitro, hydroxyl, optionally protected amino, carboxyl, oxo, optionally halo-substituted $C_{2-4}$ acylamino, and $C_{2-4}$ acyl.

In the above formulas, concrete examples of the $C_{1-12}$ alkyl are methyl, trifluoromethyl, ethyl, n-propyl, isopropyl, n-butyl, isobutyl, sec-butyl, tert-butyl, pentyl, isopentyl, hexyl, isohexyl, heptyl, 3-heptyl, octyl, nonyl, decyl, undecyl, dodecyl and cyclohexyl.

In the above formulas, concrete examples of the $C_{1-6}$ lower alkyl are methyl, trifluoromethyl, ethyl, n-propyl, isopropyl, n-butyl, isobutyl, sec-butyl, tert-butyl, pentyl, isopentyl, hexyl and isohexyl.

In the above formulas, examples of the $C_{1-3}$ lower alkyl are methyl, trifluoromethyl, ethyl, n-propyl and isopropyl.

In the above formulas, examples of the $C_{1-3}$ lower alkoxy are methoxy, ethoxy, n-propoxy and isopropoxy.

In the above formulas, concrete examples of the halogen are chlorine, bromine, iodine and fluorine.

In the above formulas, examples of the $C_{1-3}$ lower alkylsulfonyl are methylsulfonyl, ethylsulfonyl, n-propylsulfonyl and isopropylsulfonyl.

In the above formulas, concrete examples of the $C_{2-4}$ acylamino are acetylamino, propionylamino, n-butyrylamino and isobutyrylamino.

In the above formulas, concrete examples of the $C_{2-10}$ acyloxy are acetoxy, n-propionyloxy, n-butyryloxy, isobutyryloxy, n-pentanoyloxy, n-hexanoyloxy, n-heptanoyloxy, n-octanoyloxy, n-nonanoyloxy and n-decanoyloxy.

Referring to the acyl groups mentioned hereinbefore, concrete examples of the acyl group represented by the formula $R_6$—CO— ($R_6$ being as above defined) are 3-(2,6-dichlorophenyl)-5-methylisoxazol-4-yl-carbonyl, 4-ethyl-2,3-dioxo-1-piperazinecarbonyl and 2-oxoimidazolidin-1-yl-carbonyl.

Concrete examples of the acyl group represented by the formula $R_7$—NH—CH($R_9$)—CO— ($R_7$ and $R_9$ being as above defined) are D-alanyl, D-phenylalanyl, α-benzyl-N-carbobenzoxy-γ-D-glutamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltriptophyl-D-phenylglycyl, N-[2-amino-3-(N-methylcarbamoyl)propionyl]-D-phenylglycyl, N-[2-carbobenzoxyamino-3-(N-methylcarbamoyl)propionyl]-D-phenylglycyl, N-carbobenzoxy-D-phenylglycyl-D-phenylglycyl, 2-(2,3-diaminopropionamido)-2-phenylacetyl, D-alanyl-D-alanyl, 2-[2-amino-3-(N-methylcarbamoyl)propionamido]acetyl, 2-(2-amino-3-sulfamoylpropionamido)-2-phenylacetyl, 2-[2-amino-3-(4-ethyl-2,3-dioxo-1-piperazinecarboxamido)propionamido]-2-phenylacetyl, D-2-(4-ethyl-2,3-dioxo-1-piperazinecarboxamido)-2-(4-methoxyphenyl)acetyl, D-2-[2-(4-ethyl-2,3-dioxo-1-piperazinecarboxamido)-3-(N-methylcarbamoyl)propionamido]-2-phenylacetyl, D-2-[2-(4-ethyl-2,3-dioxo-1-piperazinecarboxamido)acetamido]-2-phenylacetyl, D-2-(3-sulfamoyl-2-benzyloxycarboxamidopropionamido)-2-phenylacetyl, D-2-[2-benzyloxycarboxamido-3-(4-methoxyphenyloxycarboxamido)propionamido]-2-phenylacetyl, 2-[2-benzyloxycarboxamido-3-(N-methylcarbamoyl)propionamido]acetyl, 2-(N-carbobenzoxy-D-phenylglycylamino)-3-(N-methylcarbamoyl)propionyl, N-carbobenzoxy-D-alanyl, 2-benzyloxycarboxamido-3-N-methylcarbamoylpropionyl, D-2-[2-(4-ethyl-2,3-dithioxo-1-piperazinecarboxamido)-2-phenylacetyl, 2-(2-aminothiazol-4-yl)-2-(4-ethyl-2,3-dioxo-1-piperazinecarboxamido)acetyl, 2-(2-phenylacetamido)-propionyl, 2-(4-ethyl-2,3-dioxo-1-piperazinecarboxamido-2-thienylacetyl, D-2-(4-n-dodecyl-2,3-dioxo-1-piperazinecarboxamido)-2-phenylacetyl, D-2-(4,6-dienyl-2,3-dioxo-1-piperazinecarboxamido)-2-phenylacetyl, D-2-(4-cyclohexyl-2,3-dioxo-1-piperazinecarboxamido)-2-phenylacetyl, D-2-(4-cyclohexyl-2,3-dioxo-1-piperazinecarboxamido)-2-thienylacetyl, D-2-(4-N-amyl-6(S)-methyl-2,3-dioxo-1-piperazinecarboxamido)-2-thienylacetyl, D-2-(4-ethyl-5(R)-methyl-2,3-dioxo-1-piperazinecarboxamido)-2-thienylacetyl, D-2-(4-ethyl-5(S)-methyl-2,3-dioxo-1-piperazinecarboxamido)-2-thienylacetyl, 2-(8-hydroxy-1,5-naphthyridine-7-carboxamido)-2-phenylacetyl, 2-(4-n-octyl-2,3-dioxo-1-piperazinecarboxamido)-2-phenylacetyl, 2-(4-ethyl-2,3-dioxo-1-piperazinecarboxamido)-2-(4-hydroxysulfonyloxyphenyl)acetyl, 2-(4-ethyl-2,3-dioxo-1-piperazinecarboxamido)-2-(4-chlorophenyl)acetyl, 2-(4-n-octyl-2,3-dioxo-1-piperazinecarboxamido)-2-(4-hydroxysulfonyloxyphenyl)acetyl, 2-(4-ethyl-2,3-dioxo-1-piperazinecarboxamido)-2-(4-trimethylsilylphenyl)acetyl, 2-(4-ethyl-2,3-dioxo-1-piperazinecarboxamido)-2-(3-chloro-4-methoxyphenyl)acetyl, 2-(4-ethyl-2,3-dioxo-1-piperazinecarboxamido)-2-(3-chloro-4-hydroxysulfonyloxyphenyl)acetyl, 2-(4-ethyl-2,3-dioxo-1-piperazinecarboxamido)-2-(3-chloro-4-hydroxyphenyl)acetyl, 2-(4-ethyl-2,3-dioxo-1-piperazinecarbonyl)-2-(4-benzyloxyphenyl)acetyl, 2-(4-n-octyl-2,3-dioxo-1-piperazinecarboxamido)-2-(4-hydroxyphenyl)acetyl, α[N-(4-ethyl-2,3-dioxo-1-piperazinecarbonyl)glutaminyl, N-(4-ethyl-2,3-dioxo-1-piperazinecarbonyl)phenylalanyl, N-(4-ethyl-2,3-dioxo-1-piperazinecarbonyl)-D-alanyl, 2-(4-ethyl-2,3-dioxo-1-piperazinecarboxamido)-2-(4-hydroxyphenyl)acetyl, 2,2-bis-(4-ethyl-2,3-dioxo-1-piperazinecarboxamido)acetyl, 2-(4-ethyl-2,3-dioxo-1-piperazinecarboxamido)-2-(1-cyclohexen-1-yl)acetyl, 2-(4-n-octyl-2,3-dioxo-1-piperazinecarboxamido)-2-thienylacetyl, 2-(4-ethyl-2,3-dioxo-1-piperazinecarboxamido)-2-(2-chloroacetamidothiazol-4-yl)acetyl, 2-(4-ethyl-2,3-dioxo-1-piperazinecarboxamido)-2-(2-methylthiazol-4-yl)acetyl, 2-(4-ethyl-2,3-dioxo-1-piperazinecarboxamido)-2-(2-acetamidothiazol-4-yl)acetyl, 2-(4-n-octyl-2,3-dioxo-1-piperazinecarboxamido)-2-(2-aminothiazol-4-yl)acetyl, 2-(4-ethyl-2,3-dioxo-1-piperazinecarboxamido)-2-furylacetyl, 2-(4-ethyl-2,3-dioxo-1-piperazinecarboxamido)-2-(2-pyrrolyl)acetyl, 2-(4-ethyl-2,3-dithioxo-1-piperazinecarboxamido)-2-(4-hydroxyphenyl)acetyl, 2-(4-n-octyl-2,3-dioxo-1-piperazinecarboxamido)-2-(2-chloroacetamidothiazol-4-yl)acetyl, N-(4-ethyl-2,3-dioxo-1-piperazinecarbonyl)-D-methionyl, D-2-[4-(2-phenylethyl)-2,3-dioxo-1-piperazinecarboxamido]phenylacetyl, D-2-(4-ethyl-2,3-dioxo-1-piperazinecarboxamido)-2-(4-benzoyloxyphenyl)acetyl, 2,5-bis(4-ethyl-2,3-dioxo-1-piperazinecarboxamido)pentanoyl, 2-(4-ethyl-2,3-dioxo-1-piperazinecarboxamido)-3-(N-methylcarbamoyl)propionyl, 2,3-bis-(4-ethyl-2,3-dioxo-1-piperazinecarboxamido)propionyl, 2-(4-ethyl-2,3-dioxo-1-piperazinecarboxamido)-3-chloropropionyl, 2-(4-ethyl-2,3-dioxo-1-piperazinecarboxamido)-2-(4-n-octanoyloxyphenyl)acetyl, 2-(4-ethyl-2,3-dioxo-1-piperazinecarboxamido)-3-sulfamoylpropionyl, 3-[2-(4-ethyl-2,3-dioxo-1-piperazinecarboxamido)-3-[(1-methyl-1H-tetrazol-5-yl)thio]propionyl, 2-(4-ethyl-2,3-dioxo-1-piperazinecarboxamido)acetyl, D-2-[4-(2-hydroxyethyl)-2,3-dioxo-1-piperazinecarboxamido]-2-phenylacetyl, D-2-[4-(2-chloroethyl)-2,3-dioxo-1-piperazinecarboxamido]-2-phenylacetyl, 2-(4-ethyl-2,3-dioxo-1-piperadinecarboxamido)-3-(ethoxycarbonylmethylcarbamoyl)propionyl, 2-(4-ethyl-2,3-dioxo-1-piperazinecarboxamido)-3-(thienylacetamido)propionyl, 2-(4-ethyl-2,3-dioxo-1-piperazinecarboxamido)-3-[2-(1H-tetrazol-1-yl)acetamido]propionyl, 2-(4-ethyl-2,3-dioxo-1-piperazinecarboxamido)-2-(1H-tetrazol-1-yl)acetyl, 2-[3-(furfurylideneamino-2-oxoimidazolidin-1-yl)carboxamido]-2-phenylacetyl, 2-[(3-furfurylideneamino-2-oxoimidazolidin-1-yl)carboxamido]-2-(4-hydroxyphenyl)acetyl, 2-[(3-furfurylydeneamino-2-oxoimidazolidin-1-yl)carboxamido]-2-(4-hydroxysulfonyloxyphenyl)acetyl, 2-[[2-oxo-3-(thiophene-2-aldoimino)imidazolidin-1-yl]carboxamido]-2-phenylacetyl, 2-[(3-furfurylideneamino-2-oxoimidazolidin-1- yl)carboxamido]-2-thienylacetyl, 2-[(3-methylsulfonyl-2-oxoimidazolidin-1-yl)carboxamido]-2-phenylacetyl, 2-[(3-furfurylideneamino-2-oxoimidazolidin-1-yl)carboxamido]-2-(2-aminothiazol-4-yl)acetyl, 2-[(3-furfurylideneamino-2-oxoimidazolidin-1-yl)carboxamido]-2-(2-chloroacetamidothiazol-4-yl)acetyl, 2-[[2-oxo-3-(thiophene-2-aldoimino)imidazolidin-1-yl]carboxamido]-2-thienylacetyl, 2-[(3-mesyl-2-oxoimidazolidin-1-yl)carboxamido]-2-thienylacetyl, D-2-[(3-furfurylideneamino-2-oxoimidazolidin-1-yl)carboxamido]-propionyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, D-3-[(2-oxo-3-sulfoimidazolidin-1-yl)carboxamido]-2-thienylacetyl, D-2-[(5-methoxycarbonyl-3-methyl-2-oxoimidazolidin-1-yl)carboxamido]-2-phenylacetyl, D-2-[(5-benzyloxycarbonyl-3-methyl-2-oxoimidazolidin-1-yl)carboxamido]-2-phenylacetyl, D-2-[(5-carboxy-3-methyl-2-oxoimidazolidin-1-yl)carboxamido]-2-phenylacetyl, 2-(coumarin-3-carboxamido)-2-phenylacetyl, 2-(4-ethyl-2,3-dioxo-1-piperazinecarboxamido)-2-(2-chloro-1-cyclohexen-1-yl)acetyl, D-2-(4-n-amyl-2,3-dioxo-1-piperazinecarboxamido)-2-phenylacetyl, D-2-(4-n-amyl-6(R)-methyl-2,3-dioxo-1-piperazinecarboxamido)-2-thienylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-aminothiazol-4-yl)acetyl]-D-phenylglycyl, 2-(6-bromo-1-ethyl-1,4-dihydro-4-oxothieno[2,3-b]pyridine-3-carboxamido)-2-phenylacetyl, 2-[2-(2-chloroacetamidothiazol-4-yl)acetamido]-2-phenylacetyl, 2-(2,5-dioxo-1,2,4-triazine-6-carboxamido)-2-thineylacetyl, 2-(2,4-dioxopyrimidine-5-carboxamido)-2-thienylacetyl, 2-[2-(4-ethyl-2,3-dioxo-1-piperazinecarboxamido)-2-thienylacetamido]phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxypropylamino)-2-furylacetyl, α-(thienylmethylcarbonyl)alanyl, 2-(4-chlorobenzoylureido)-2-thienylacetyl, 2-(2-thienylacetamido)acetyl, N-benzyloxycarboxamido-D-alanyl, N-(4-hydroxybenzoyl-D-alanyl, 2-(4-chlorobenzamido)propionyl, 2-(4-aminobenzamido)acetyl, N-(4-ethyl-2,3-dioxo-1-piperazinecarbonyl)methionyl-D-phenylglycyl, D-2-[[3-(2,6-dichlorophenyl)-5-methylisoxazol-4-yl]carboxamido]-2-thienylacetyl, 2-ureido-2-thienylacetyl, N-carbamoyl-D-phenylglycyl, 2-(3-methylcarbamoyl-3-methyl-1-ureido)-2-phenylacetyl, 2-(3-methylcarbamoyl-3-methyl-1-ureido)-2-(4-hydroxyphenyl)acetyl, 2-(3-methylcarbamoyl-3-methyl-1-ureido)-2-thienylacetyl, 2-[3-(2-hydroxybenzoyl)-1-ureido]-2-phenylacetyl, 2-[3-(2-benzyloxybenzoyl)-1-ureido]-2-(4-hydroxysulfonyloxyphenyl)acetyl, 2-[3-(2-hydroxybenzoyl)-1-ureido]-2-(4-hydroxyphenyl)acetyl, 2-[3-(2-benzyloxybenzoyl)-1-ureido]-2-phenylacetyl, 2-[3-(2-benzyloxybenzoyl)-1-ureido]-2-(4-hydroxyphenyl)acetyl, D-2-[2-(benzyloxycarboxamido)-2-(benzyloxycarbonyl)ethanesulfonamido]-2-phenylacetyl, N-mesyl-D-phenylglycyl, 2-(2-aminothiazol-4-yl)-2-ureidoacetyl, 2-(2-aminothiazol-4-yl)-2-formamidoacetyl, 2-(2-aminothiazol-4-yl)-2-acetamidoacetyl, 2-(2-aminothiazol-4-yl)-2-[(1-carboxy-1-methylethoxy)imino]acetyl, 2-(2-aminothiazol-4-yl)-2-pivalamidoacetyl, 2-(2-aminothiazol-4-yl)-2-[2-(methoxycarbonyl)acetamido]acetyl, 2-(2-aminothiazol-4-yl)-2-[[3-(3-thienylidene)amino-2-oxoimidazolydin-1-yl]carboxamido]acetyl, 2-thienyl-2-[[3-(3-thienylidene)amino-2-oxoimidazolydin-1-yl]carboxamido]acetyl, 2-(2-aminothiazol-4-yl)-2-(oxamoylamino)acetyl, 2-(2-aminothiazol-4-yl)-2-(methoxalylamino)acetyl, 2-(2-aminothiazol-4-yl)-2-(oxaloamino)acetyl, etc.

Examples of the acyl group of the formula $R_{10}-R_{11}-CO-$ ($R_{10}$ and $R_{11}$ being as above defined) are N-[2-(2-aminothiazol-4-yl)-2-methoxyiminoacetyl]-D-alanyl, N-[2-(2-aminothiazol-4-yl)-2-methoxyiminoacetyl]-D-phenylglycyl, 2-(2-aminothiazol-4-yl)-2-[2-(2-aminothiazol-4-yl)-2-methoxyiminoacetamido]acetyl, 2-(2-chloroacetamidothiazol-4-yl)-2-[2-(2-chloroacetamidothiazol-4-yl)-2-methoxyiminoacetamido]acetyl, 2-(2-chloroacetamidothiazol-4-yl)-2-methoxyiminoacetyl, 2-(2-aminothiazol-4-yl)-2-(1-methylethoxyimino)acetyl, 2-(2-aminothiazol-4-yl)-2-methoxyiminoacetyl, 2-(2-aminothiazol-4-yl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-(dichloroacetyloxyimino)acetyl, 2-[4-(γ-D-glutamyloxy)phenyl]-2-oxyiminoacetyl, 2-[4-(3-amino-3-carboxypropoxy)phenyl]-2-oxyiminoacetyl, 2-thienyl-2-(3-morpholinopropyloxyimino)acetyl, 2-(5-chloro-2-chloroacetamidothiazol-4-yl)-2-methoxyiminoacetyl, 2-(5-chloro-2-aminothiazol-4-yl)-2-methoxyiminoacetyl, 2-(2-aminothiazol-4-yl)-2-[(1-carboxy-1-methylethoxy)imino,2-[(1-t-butoxycarbonyl-1-methyl)ethoxyimino]-2-(2-hydroxysulfonylaminothiazol-4-yl)acetyl, 2-[(1-t-butoxycarbonyl-1-methyl)ethoxyimino]-2-(2-triphenylmethylaminothiazol-4-yl)acetyl, 2-(2-chloroacetamidothiazol-4-yl)-2-(1-methylethoxyimino)acetyl, 2-methoxyimino-2-(2-sulfoaminothiazol-4-yl)acetyl, 2-[2-(2-chloroacetamidothiazol-4-yl)-2-methoxyiminoacetamido]-2-phenylacetyl, 2-[2-(2-aminothiazol-4-yl)-2-methoxyiminoacetamido]acetyl, 2-(2-mesylaminothiazol-4-yl)-2-(1-methylethoxyimino)acetyl, and 2-(2-imino-3-mesyl-4-thiazolin-4-yl)-2-(1-methylethoxyimino)acetyl, 2-(2-aminothiazol-4-yl)-2-[(carboxy)methoxyimino]acetyl, 2-(2-aminothiazol-4-yl)-2-[(1-carboxy)ethoxyimino]acetyl, 2-(2-aminothiazol-4-yl)-2-[(1-carbamoyl-1-methylethoxy)imino]acetyl, 2-(2-aminothiazol-4-yl)-2-[(1-methoxycarbonyl-1-methyl)ethoxyimino]acetyl, 2-(2-aminothiazol-4-yl)-2-[(tetrazol-5-yl)methoxyimino]acetyl, 2-(2-aminothiazol-4-yl)-2-[(methoxycarbonyl)methoxyimino]acetyl, etc.

Concrete examples of the acyl group represented by the formula

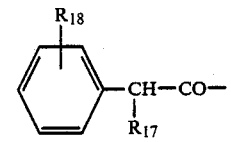

wherein $R_{17}$ and $R_{18}$ are as above defined, are α-sulfophenylacetyl, α-hydroxysulfonyloxyphenylacetyl, α-hydroxyphenylacetyl, α-sulfamoylphenylacetyl, α-(phenoxycarbonyl)phenylacetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl, 2-bromo-2- phenylacetyl, 2-azido-2-phenylacetyl, 2-phthalimido-2-thienylacetyl and 2-azido-2-(3-chlorophenyl)acetyl, etc.

Concrete examples of the acyl group represented by the formula $R_{19}-R_{20}-CH_2-CO-$, wherein $R_{19}$ and $R_{20}$ are as above defined, are cyanoacetyl, phenylacetyl, phenoxyacetyl, trifluoromethylthioacetyl, cyanomethylthioacetyl, 1H-tetrazol-1-ylacetyl, 2-thienylacetyl, 2-(2-aminothiazol-4-yl)acetyl, 2-(2-chloroacetamidothiazol-4-yl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-[[2-(2-oxoimidazolidin-1-yl)carboxamidomethyl]phenyl]acetyl, 2-[2-(3-benzylideneamino-2-oxoimidazolidin-1-yl)carboxamidomethylphenyl]acetyl, 2-(5,6-dihydro-1,4-oxatiin-2-yl)acetyl, 2-(2,5-dioxopyrrolidin-3-yl)acetyl, 2-succinimidoacetyl and 2-(1-acetyl-2,4-dioxoimidazolidin-3-yl)acetyl.

The amino and/or carboxyl group in the above acyl group may be protected with a protective group.

Said amino-protecting group includes those mentioned as examples of the "amino-protecting group" mentioned hereinafter.

Said carboxyl-protecting group includes all groups that can commonly be used as carboxyl-protecting groups in the field of β-lactam and organic chemistry, such as esters or silyl ester whose ester moieties are, for example, methyl, ethyl, propyl, isopropyl, tert-butyl, tert-amyl, benzyl, p-nitrobenzyl, p-methoxybenzyl, benzhydryl, phenacy, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, 2-trimethylsilylethyl trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminomethyl, pyridine-1-oxide-2-methyl, methylsulfinylmethyl, bis(p-methoxyphenyl)-methyl and 2-cyano-1,1-dimethylethyl. Since the present invention is to provide the above-mentioned novel monocyclic compounds, selection of said protective group is not critical. Especially benzyl, β,β,β-trichloroethyl, p-nitrobenzyl, p-methoxybenzyl benzhydryl, 2-trimethylsilylethyl, and t-butyl are preferred.

As the amino-protecting group in the above general formula, there may be adequately be employed those used for amino protection in the field of β-lactam and peptide synthesis. For example, there may be used aromatic acyl groups (e.g. phthaloyl, p-nitrobenzoyl, p-tert-butylbenzoyl, p-tert-butylbenzenesulfonyl, benzenesulfonyl, toluenesulfonyl), aliphatic acyl groups (e.g. formyl, acetyl, propionyl, monochloroacetyl, dichloroacetyl, trichloroacetyl, methanesulfonyl, ethanesulfonyl, trifluoroacetyl, maloyl, succinyl), esterified carboxyl groups (e.g. 2-trimethylsilylethoxycarbonyl, benzyloxycarbonyl, p-nitrobenzyloxycarbonyl, p-methoxybenzyloxycarbonyl, methoxycarbonyl, ethoxycarbonyl, tert-butoxycarbonyl, isopropoxycarbonyl, 2-cyano-ethoxycarbonyl, β,β,β-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl), methylene groups (e.g. (hexahydro-1H-azepin-1-yl)methylene), sulfonyl groups (e.g. 2-amino-2-carboxyethylsulfonyl), and further other aminoprotecting groups than acyl groups (e.g. trityl, 2-nitrophenylthio, benzylidene, 4-nitrobenzylidene, di- or trialkylsilyl, benzyl, p-nitrobenzyl).

Referring to the optionally acylated or protected amino group represented by $R_1$ in the above general formula, said $R_1$, from the view point of the production of β-lactamase inhibitors, may preferably have the formula

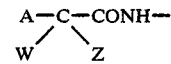

In the formula, A is hydrogen, lower alkyl (e.g. methyl, ethyl, isobutyl), alicyclic group (e.g. cyclohexyl, cyclohexenyl), aryl (e.g. phenyl), aralkyl (e.g. benzyl) or heterocyclic group (e.g. thienyl, benzothienyl, pyrrolyl, isoxazolyl, piperazinyl, thiazolyl, tetrazolyl, oxathiano). Said A may have one or two substituents, such as amino, lower alkyl, lower alkoxy, phenyl, 2,6-dichlorophenyl, oxo, hydroxyl, halogen, chloroacetamido, etc. Z is hydrogen, and W is hydrogen, optionally esterified carboxyl, sulfo, sulfamoyl, hydroxysulfonyloxy, optionally protected amino, arylcarboxamido (e.g. phenylcarboxamido), lower alkylcarboxamido, other amido, or heterocycle-carboxamido [e.g. (2,3-dioxo-1-piperazine)carboxamido, imidazolidinecarboxamido, oxoimidazolidinecarboxamido, (1,2-diazole)-carboxamido, (isoxazol-4-yl)carboxamido, (2-aminothiazol-4-yl)methylcarboxamido, 3-(2,3-dioxo-1-piperazinecarboxamido)-2-carbobenzoxyaminopropionamido], or W and Z combinedly represent a group represented by the formula N-X'-G, wherein X' is oxygen, sulfur or sulfoxide group, G is lower alkyl, carboxy-lower alkyl (e.g. α,α-dimethyl-α-carboxymethyl whose carboxyl may optionally be protected), aryl (e.g. phenyl) or acyl (e.g. acetyl). Furthermore,

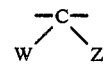

may represent a mere single bond or

In the above formula, the lower alkyl represented by A is preferably a straight-chained or branched $C_{1-4}$ alkyl, which may be substituted by the above-mentioned substituents and/or by N-methylcarbamoyl, carbobenzyloxyamino, aryl (e.g. phenyl), tetrazolylacetamido, 4-ethyl-2,3-dioxo-1-piperazine carboxamido, heterocyclic group (e.g. 1,2-diazole optionally substituted by phenyl, methyl or ethyl at the 3-position), etc.

The halogen, which is an optional substituent on A, includes fluorine, chlorine, bromine, etc., the lower alkyl includes methyl, ethyl, etc., and the lower alkoxy includes methoxy, ethoxy, etc.

The optionally protected amino group represented by W includes chloroacetylamino, aralkylamino, aralkyloxycarbonylamino, among others.

The heterocycle-carboxamido group represented by W may have one or two substituents, which includs among others phenyl, $C_{1-12}$ alkyl, saturated alicyclic group, $C_{2-8}$ alkenyl, aryl-carbonyl optionally having lower alkoxy such as methoxy or ethoxy, furfurylideneamino, sulfo, alkoxycarbonyl, aralkyloxycarbonyl and carboxyl.

The lower alkyl of the lower alkyl-carboxamido group represented by W is preferably a straight chained or branched $C_{1-4}$ alkyl, which may be substituted by halogen (e.g. chlorine, bromine, fluorine), sulfamoyl and/or optionally protected amino. Said sulfamoyl may be substituted by sulfo.

Preferable $R_1$ may be a group of the formula

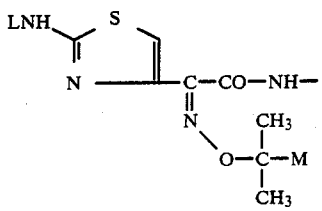

wherein L is sulfo, lower alkylsulfonyl or trityl and M is hydrogen or esterified carboxyl.

The compounds (I) of the present invention can be produced, for example by reacting a compound of the formula

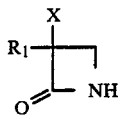

(II)

wherein $R_1$ and X are as above defined, with sulfuric anhydride or a reactive derivative thereof, for instance.

Said reactive derivative of sulfuric anhydride includes among others such adducts as sulfuric anhydride-pyridine, sulfuric anhydride-dimethylformamide, sulfuric anhydride-dioxane, sulfuric anhydride-trimethylamine and sulfuric anhydride-chlorosulfonic acid.

The above reaction is carried out by adding, to one mole of compound (II), about 1 to about 5, preferably about 1 to about 2 moles of sulfuric anhydride or a reactive derivative thereof.

The reaction temperature is about 0° C. to about 80° C., preferably about 10° C. to about 40° C. In carrying out the above reaction, a solvent may be used. Usable solvents are water, ethers (e.g. dioxane, tetrahydrofuran, diethyl ether), esters (e.g. ethyl acetate, ethyl formate), halogenated hydrocarbons (e.g. chloroform, methylene chloride), hydrocarbons (e.g. benzene, toluene, n-hexane), amides (e.g. dimethylformamide, dimethylacetamide) and other common organic solvents, either alone or in combination. After the reaction, the compounds (I) of any desired purity can be obtained by subjecting the reaction mixture to a purification/isolation process known per se, such as solvent extraction, recrystallization and/or chromatography.

Among the starting compounds (II) to be used in the synthesis of the compounds (I), those wherein X is a hydrogen atom are described in Japanese Published unexamined patent application No. 125,061/76 through No. 125,064/76, (the corresponding British Pat. No. 1519495) for instance. These compounds, including the compounds wherein X is a methoxy group, can be produced, for example, by oxidizing a compound of the general formula

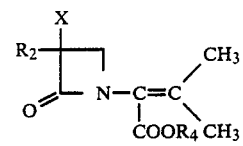

(III)

with ozone, an alkali metal permanganate (e.g. potassium permanganate, sodium permanganate), an alkaline earth metal permanganate (e.g. barium permanganate), osmium tetrachloride or lead tetraacetate etc., for instance, in tetrahydrofuran, dioxane, N,N-dimethylformamide, N,N-dimethylacetamide, benzene, acetone, pyridine, methanol, ethanol, propanol, butanol, water, chloroform, dichloromethane or carbon tetrachloride, or a mixture thereof. Among the above compounds (III), those wherein X is a methoxy group can be produced by reacting a corresponding compound wherein X is a hydrogen atom with lithium, sodium or potassium methoxide and a halogenating agent such as a halogen (e.g. chlorine, bromine), an N-haloimide (e.g. N-chlorosuccinimide, N-bromosuccinimide), an N-haloamide (e.g. N-chloroacetamide, N-bromoacetamide), an N-halosulfonamide (e.g. N-chlorobenzenesulfonamide, N-chloro-p-toluenesulfonamide), a 1-halobenzotriazole or an organic hypochlorite (e.g. tert-butyl hypochlorite), in the presence of methanol, for example in tetrahydrofuran, dioxane, methylene chloride, chloroform, acetonitrile, methanol, N,N-dimethylformamide or N,N-dimethylacetamide, or a mixture thereof. The compounds (II) may be subjected to the reaction in the form of salts with various acids or bases, esters or silyl derivatives.

Those compounds (II) wherein $R_1$ is an amino group can be converted to the compounds (II) wherein $R_1$ is an acylated amino group by acylation in a conventional manner.

The compounds (I) of the present invention, when they have a protective group, can be converted to the compounds (I) which have no protective group by removal of said protective group. The compounds (I) can form salts by reaction with bases or acids. Therefore, the compounds (I) may be collected as salts, and the salts obtained may be converted to the free form or to different salts. Furthermore, the compounds (I) obtained in the free form may be converted to salts. Examples of the above-mentioned bases are inorganic bases such as lithium, potassium, sodium, calcium and ammonia, and organic bases such as pyridine, colidine, triethylamine, triethanolamine and tetrabutylammonium hydroxide. Examples of the acids are inorganic acids such as hydrochloric acid, sulfuric acid and phosphoric acid etc., and organic acids such as acetic acid, succinic acid, propionic acid, mandelic acid, citric acid and tartaric acid, etc. The salts with these acids or bases are all stable, occur as powders, are almost tasteless and odorless, and have little toxicity ($LD_{50}$ values in rats being 2 g or higher).

In some cases, the compounds (I) comprise optical isomers (e.g. D-isomer, L-isomer). In these cases, the individual isomers as well as mixtures thereof fall under the scope of the present invention.

The inhibitors of the present invention are used in administering β-lactam antibiotics, for treatment or prevention of bacterial infections in humans and domestic animals.

The inhibitors of the present invention, when alone made into pharmaceutical preparations, are used before or after administration of β-lactam antibiotics, or are mixed with said antibiotics prior to use. Said β-lactam antibiotics include among other benzylpenicillin, phenoxymethylpenicillin, sulbenicillin, carbenicillin, ampicillin, amoxicillin, mecillinam, cloxacillin, dicloxacillin, piperacillin, apalcillin, ticarcillin, cephaloridine, cephalothin, cefazolin, cefalexin, cefacetril, cefamandolenafate, cefuroxime, cefotiam, cefoxitin, cefmetazole, cefsulodin, cefaclor, cefatrizine, cefotaxime, cefmenoxime, ceftazidine, ceftizoxime, and other known penicillins and cephalosporins, as well as hetacillin, metampicillin, talampicillin, carindacillin, carfecillin, pivmecillinam, etc. Dosage forms, such as injections, dry syrrups, granules, tablets and capsules, are prepared in a conventional manner. Preferred is the salt or hydrate form for injection.

The compounds (I) of the present invention can be used in a weight ratio of 10:1 to 1:10 based on the β-lactam antibiotics. Advantageous is a ratio of 1:1 to 1:8, for example, 1:2, 1:3, 1:4, 1:5 or 1:6.

The compounds of the present invention are generally administered at a daily dose of 50–1,000 mg. Usually, a daily dose of 100–750 mg is administered, for example, by one to six, usually two to four administrations.

The β-lactam antibiotics are used in the synergistic compositions of the present invention in amounts generally recognized as appropriate or less.

TEST EXAMPLE 1

Determination of the inhibitor concentration required to inhibit the enzyme activity by 50%

The β-lactamase produced by *Enterobacter cloacae* IFO 12937 is used as a typical example of cephalosporinase, and that produced by *Staphylococcus aureus* 1840 as typical example of penicillinase. The β-lactamase in incubated is 0.05M phosphate buffer (pH 7) with an appropriate dilution of an inhibitor preparation at 30° C. for 10 minutes. Cephalothin or ampicillin is then added in an amount sufficient to produce a final concentration of 0.1 mM, and the enzymatic reaction is allowed to proceed for 10 minutes. The enzyme activity is determined by the micro-iodometric method [Journal of general Microbiology, vol. 33, page 121 (1963)]. Hereinafter, the inhibitor concentration required to inhibit the enzyme activity by 50% is expressed as $I_{50}$. The $I_{50}$ values for *Enterobacter cloaceae* are shown in Table 1, and the $I_{50}$ values for *Staphylococcus aureus* in Table 2.

TABLE 1

| Compound No. | $R_1$ | X | $I_{50}$ (μg/ml) |
|---|---|---|---|
| 1 | 2-(4-n-octyl-2,3-dioxo-1-piperazine-carboxamido)-2-thienylacetamido | H (hydrogen) | 2.8 |
| 2 | 2-(4-n-octyl-2,3-dioxo-1-piperazine-carboxamido)-2-thienylacetamido | methoxy | 0.046 |
| 3 | D-2-[(2-oxo-3-furfurylideneamino-imidazolidin-1-yl)carboxamido]-2-phenylacetamido | methoxy | 0.33 |
| 4 | 2-benzyloxycarbonyl-2-phenylacetamido | methoxy | 0.04 |
| 5 | 2-carboxy-2-phenylacetamido | methoxy | 0.14 |
| 6 | 2-benzyloxycarboxamido-3-(N—methylcarbamoyl)propionamido | methoxy | 1.1 |

TABLE 1-continued

| Compound No. | $R_1$ | X | $I_{50}$ (μg/ml) |
|---|---|---|---|
| 7 | D-N—(4-ethyl-2,3-dioxo-1-piperazine-carbonyl)phenylalanylamino | methoxy | 1.1 |
| 8 | D-N—carbobenzoxyalanylamino | methoxy | 3.2 |
| 9 | [3-(2,6-dichlorophenyl)-5-methyl-isoxazol-4-yl]carboxamido | H | 0.068 |
| 10 | 2-(4-ethyl-2,3-dioxo-1-piperazine-carboxamido)-2-(1-cyclohexen-1-yl)-acetamido | H | 2.3 |
| 11 | N—2-(4-ethyl-2,3-dioxo-1-piperazine-carboxamido)-2-phenylacetamido | methoxy | 0.26 |
| 12 | 2-(2-aminothiazol-4-yl)-2-methoxy-iminoacetamido | H | 1.4 |
| 13 | 2-(2-aminothiazol-4-yl)-2-methoxy-iminoacetamido | methoxy | 0.27 |
| 14 | 2-(2-chloroacetamidothiazol-4-yl)-2-methoxyiminoacetamido | methoxy | 0.3 |
| 15 | 2-hydroxysulfonyloxy-2-phenyl-acetamido | H | 3.6 |
| 16 | 2-methoxyimino-2-phenylacetamido | H | 5.0 |
| 17 | 2,6-dimethoxybenzoylamino | H | 2.5 |
| 18 | 2,6-dimethoxybenzoylamino | methoxy | 1.8 |
| 19 | 2-(5-chloro-2-chloroacetamido-thiazol-4-yl)-2-methoxyimino-acetamido | H | 0.3 |
| 20 | 2-(2-amino-5-chlorothiazol-4-yl)-2-methoxyiminoacetamido | H | 1.2 |
| 21 | 2-phenyl-2-p-tolylthioiminoacetamido | H | 0.55 |
| 22 | 2-(4-ethyl-2,3-dioxo-1-piperazine-carboxamido)-2-(2-chloro-1-cyclohexen-1-yl)acetamido | H | 3.0 |
| 23 | 2-(2-aminothiazol-4-yl)-2-(1-methyl-ethoxyimino)acetamido | H | 0.020 |
| 24 | 2-[3-(N—sulfosulfamoyl)-2-carbo-benzoxyaminopropionamido]propionamido | methoxy | 0.76 |
| 25 | 2-[3-(2,6-dichlorophenyl)-5-methyl-isoxazol-4-yl]carboxamido-2-thienyl-acetamido | H | 3.6 |
| 26 | 2-[(1-t-buthoxycarbonyl-1-methylethoxy)imino]-2-(2-sulfoaminothiazol-4-yl)acetamido | H | 0.0055 |
| 27 | 2-[(1-t-buthoxycarbonyl-1-methylethoxy)imino]-2-(2-triphenylmethyl-aminothiazol-4-yl)acetamido | H | 0.050 |
| 28 | 2-(2-chloroacetamidothiazol-4-yl)-2-(1-methylethoxyimino)acetamido | H | 1.10 |
| 29 | 2-methoxyimino-2-(2-sulfoaminothiazol-4-yl)acetamido | H | 0.07 |
| 30 | carbobenzoxyamino | methoxy | 5.0 |
| 31 | 2-(2-aminothiazol-4-yl)-2-(1-methylethoxyimino)acetamido | H | 0.020 |
| 32 | 2-(2-mesylaminothiazol-4-yl)-2-(1-methylethoxyimino)acetamido | H | 0.0021 |
| 33 | 2-(2-imino-3-mesyl-4-thiazolin-4-yl)-2-(1-methylethoxyimino)acetamido | H | 0.0020 |
| 34 | 2-phthalimido-2-thienylacetamido | H | 0.38 |
| 35 | 2-azido-2-phenylacetamido | methoxy | 0.36 |
| 36 | 2-(2-aminothiazol-4-yl)-2-(1-methylethoxyimino)acetamido | methoxy | 0.023 |
| 37 | 2-(4-cyclohexyl-2,3-dioxo-1-piperadinecarboxamido)-2-thienylacetamido | methoxy | 0.120 |
| 38 | 2-[4-(piperidine-1-carbonyl)-2,3-dioxo-1-piperadinecarboamido]-2-thienylacetamido | methoxy | 0.078 |
| 39 | 2-(4-phenyl-2,3-dioxo-1-piperadinecarboxamido)-2-thienylacetamido | methoxy | 0.070 |
| 40 | 2-(4-t-butyl-2,3-dioxo-1-piperadinecarboxamido)-2-thienylacetamido | methoxy | 0.066 |
| 41 | 2-[4-(3-methyl-2-butenyl)-2,3-dioxo-1-piperadinecarboxamido]-2-thienylacetamido | methoxy | 0.065 |
| 42 | 2-(4-hydroxyphenyl)-2-(4-methoxy-benzyloxycarbonyl)acetamido | methoxy | 0.20 |
| 43 | 2-[(1-carboxy-1-methylethoxy)imino]-2-(2-tritylaminothiazol-4-yl)- | H | 3.2 |

TABLE 1-continued

| Compound No. | R₁ | X | $I_{50}$ (μg/ml) |
|---|---|---|---|
| | acetamido | | |

TABLE 2

| Compound No. | R₁ | X | $I_{50}$ (μg/ml) |
|---|---|---|---|
| 44 | D-2-(4-ethyl-5(S)-methyl-2,3-dioxo-1-piperazinecarboxamido)-2-thienyl-acetamido | H | 1.2 |
| 25 | D-2-[[3-(2,6-dichlorophenyl)-5-methylisoxazol-4-yl]carboxamido]-2-thienylacetamido | H | 0.4 |
| 45 | D-2-[(2-oxoimidazolidin-1-yl)-carboxamido]-2-thienylacetamido | H | 2.4 |
| 46 | D-2-(2,6-dichlorophenylthioglycol-amido)-2-phenylacetamido | H | 5.0 |
| 47 | D-2-[2-(2-aminothiazol-4-yl)acetamido]-2-phenylacetamido | H | 5.0 |
| 48 | 2-carbobenzoxyamino-2-benzyloxy-carbonylethylsulfonamido | H | 1.7 |
| 49 | 2-oxo-2-phenylacetamido | H | 4.00 |
| 50 | 2-bromo-2-phenylacetamido | H | 0.19 |
| 51 | 2-azido-2-phenylacetamido | H | 0.05 |
| 52 | mesylamino | H | 3.50 |
| 53 | 2-azido-2-(3-chlorophenyl)acetamido | H | 0.056 |
| 54 | [4-[(benzoyl)(ethoxycarbonyl)-methylene]-1,3-dithiethan-2-yl]-carboxamido | H | 1.20 |

TEST EXAMPLE 2

Synergy with Cefotiam

Cefotiam is added in accordance with a concentration gradient to an agar medium containing 1 μg/ml of a test compound, a test organism is inoculated thereon, and, after 18 hours, the minimum inhibitory concentration (MIC) is determined. The inoculum concentration is 10⁸ per ml, and the medium is prepared by using Trypticase ® soy agar (Becton Dickinson & Company, USA).

The results obtained are as shown in Tables 3 and 4.

TABLE 3

| Test organism | Cefotiam alone | With 1 μg/ml of compound No. 28 | 32 | 33 |
|---|---|---|---|---|
| *Serratia marcescens* IFO 12648 | >400 | 200 | 200 | 200 |
| *Proteus vulgaris* GN 5297 | 100 | 100 | 100 | 100 |
| *Proteus morganii* IFO 3168 | 400 | 100 | 25 | 50 |
| *Enterobacter cloacae* TN 587 | >400 | 50 | 12.5 | 3.13 |
| *Citrobacter freundii* IFO 12681 | 200 | 50 | 12.5 | 6.25 |
| *Citrobacter freundii* GN 1706 | 200 | 50 | 100 | 50 |

TABLE 4

| Test organism | Cefotiam alone | With 1 μg/ml of Compound No. 3 | 9 | 12 | 26 | 27 | 29 |
|---|---|---|---|---|---|---|---|
| *Proteus morganii* TN 387 | 200 | 0.39 | <0.2 | 25 | 0.2 | <0.2 | 100 |
| *Enterobacter cloacae* IFO 12937 | 100 | 3.13 | 0.39 | 0.2 | 0.39 | 0.39 | 0.78 |
| *Citrobacter freundii* TN 512 | 625 | 0.39 | 0.39 | <0.2 | 0.39 | 0.39 | 0.39 |
| *Citrobacter freundii* GN 1706 | 50 | 12.5 | 3.13 | 25 | 3.13 | 3.13 | 12.5 |
| *Proteus vulgaris* GN 5297 | 400 | 400 | 100 | 25 | <0.2 | <0.2 | 200 |

The following reference examples, synthesis examples and examples will illustrate the present invention in more detail. In the synthesis examples, the symbols used have the following meanings:

| | |
|---|---|
| THF | tetrahydrofuran |
| DMF | dimethylformamide |
| DMSO | dimethylsulfoxide |
| s | singlet |
| d | doublet |
| t | triplet |
| q | quartet |
| m | multiplet |
| dd | double doublet |
| ddd | sextet |
| arom. | aromatic |

REFERENCE EXAMPLE 1

To a solution of 0.104 g of 3-amino-2-oxoazetidine in 4 ml of DMF are added 0.354 g of D-N-(3-furfurylideneamino-2-oxo-1-imidazolidinecarbonyl)alanine and 0.269 g of dicyclohexylcarbodiimide, and the mixture is stirred at room temperature for 8 hours. The crystalline precipitate is filtered off, and the filtrate is concentrated. Ethyl acetate is added to the residue, and the insoluble matters are collected by filtration and washed well with ethyl acetate (or the residue is purified by silica gel column chromatography) to give 0.373 g of 3-[D-2-[(3-furfurylideneamino-2-oxoimidazolidin-1-yl)carboxamido]propionamido]-2-oxoazetidine.

$IR\nu_{max}^{KBr}$cm$^{-1}$: 3275, 1760, 1725, 1660, 1415.

REFERENCE EXAMPLE 2

6.0 g of methyl 3-benzyloxycarboxamido-3-methoxy-2-oxoazetidine-1-(α-isopropylidene)acetate are dissolved in 150 ml of methylene chloride, and ozone gas is introduced into the solution at −50° to −30° C. The reaction mixture is blue after one hour. Then, the excess ozone gas is removed by the introduction of nitrogen gas, followed by addition of dimethyl sulphide. After stirring at room temperature for an hour, the reaction mixture is washed with water and the solvent is distilled off to give 6.1 g of methyl 3-benzyloxycarboxamido-3-methoxy-2-oxoazetidine-1-α-ketoacetate. 19 ml of 0.002% sodium methoxide in methanol are added to a solution of this product in 75 ml of methanol, and the mixture is stirred at room temperature for 15 minutes.

After the addition of 0.3 g of acetic acid, the solvent is distilled off, and the residue is dissolved in ethyl acetate. The solution is washed with water, and the solvent is distilled off. The residue is chromatographed on a column of silica gel [eluted with ethyl acetate-n-hexane (1:1)] to obtain 2.7 g of 3-benzyloxycarboxamido-3-methoxy-2-oxoazetidine as crystals.

Optical rotation: $[\alpha]_D^{25} + 68.2°$ (c=1, CH$_3$OH).
IR$\nu_{max}^{CHCl_3}$cm$^{-1}$: 3420, 1774, 1723.
NMR(CDCl$_3$, ppm): 3.45(s, CH$_3$), 3.60(d, J=6 Hz, C$_4$—H), 3.80(d, J=6 Hz, C$_4$—H), 5.14(s, —CH$_2$—), 6.74(broad s, NH), 7.34(s, arom.H).

REFERENCE EXAMPLE 3

A mixture of 0.2 g of 3-benzyloxycarboxamido-3-methoxy-2-oxoazetidine and 0.50 g of palladium black in 5 ml of THF is stirred in a hydrogen gas stream for 1.5 hours. The catalyst is filtered off and the filtrate is concentrated to obtain 0.09 g of 3-amino-3-methoxy-2-oxoazetidine.

IR$\nu_{max}^{Nujol}$cm$^{-1}$: 3250, 1740.
NMR(CDCl$_3$, ppm): 2.35(broad s, NH$_2$), 3.40(dd, J=6 Hz, C$_4$—H), 3.45(s, CH$_3$), 6.7(broad s, NH).

REFERENCE EXAMPLE 4

In 20 ml of methylene chloride is dissolved 0.116 g of 3-amino-3-methoxy-2-oxoazetidine, and the solution is cooled to $-15°$ C. At this temperature, 15 ml of propylene oxide is added, and then 20 ml of a methylene chloride solution containing the acid chloride prepared from 1.06 g of D-N-(3-furfurylideneamino-2-oxo-1-imidazolidinecarbonyl)alanine is added. After stirring at the same temperature for 5 minutes, 0.712 g of pyridine is added and stirring is continued for an hour. The reaction mixture is concentrated under reduced pressure, and to the residue is added icewater, followed by extraction with chloroform. The extract is washed with water and concentrated under reduced pressure, and the residue is purified by silica gel column chromatography to give 3-[D-2-[(3-furfurylideneamino-2-oxoimidazolin-1-yl)carboxamido]propionamido]-3(S)-methoxy-2-oxoazetidine [I] and 3-[D-2-[(3-furfurylideneamino-2-oxoimidazolin-1-yl)carboxamido]-propionamido]-3(R)-methoxy-2-oxoazetidine [II].

For [I]:
IR$\nu_{max}^{KBr}$cm$^{-1}$: 3230, 1755, 1725, 1655, 1520, 1415, 1230.
NMR(DMSO-d$_6$, ppm): 1.30(d, J=7 Hz, CH$_3$), 3.35(s, OCH$_3$), 3.47(q, J=6, 8 Hz, C$_4$—H), 3.80(s, —CH$_2$—), 4.46(quintet, J=7Hz, —CH—),
|

6.5–7.9(m, arom.H), 7.73(s, —CH=N—), 8.29(s, NH), 8.44(d, J=7 Hz, NH), 9.23(s, NH).

For [II]:
IR$\nu_{max}^{KBr}$cm$^{-1}$: 3230, 1755, 1725, 1655, 1520, 1415, 1230.
NMR(DMSO-d$_6$, ppm): 1.32(d, J=7 Hz, CH$_3$), 3.36(s, —OCH$_3$), 3.50(q, J=6, 12 Hz, C$_4$—H), 3.80(s, —CH$_2$—), 4.46(quintet, J=7Hz, —CH—),
|

6.5–7.9(m, arom.H), 7.73(s, —CH=N—), 8.32(s, NH), 8.45(d, J=7 Hz, NH), 9.29(s, NH).

REFERENCE EXAMPLE 5

The compounds shown below are prepared by reacting 3-amino-2-oxoazetidine with an acylating agent and treating the reaction mixture following the procedure as described in Reference Example 1 (=A) or Reference Example 4 (=B). In the following, (a) stands for the product, (b) for the procedure used, and (c) for the physico-chemical constants for the product.

(1)
(a) 3-[D-2-(4-n-octyl-2,3-dioxo-1-piperazinecarboxamido)-2-thienylacetamido]-2-oxoazetidine
(b) A
(c) IR$\nu_{max}^{KBr}$cm$^{-1}$: 3280, 2925, 2855, 1755, 1710, 1675, 1505, 1190.

(2)
(a) 3-[D-2-(4-n-dodecyl-2,3-dioxo-1-piperazinecarboxamido)-2-phenylacetamido]-2-oxoazetidine
(b) A
(c) IR$\nu_{max}^{KBr}$cm$^{-1}$: 3280, 2920, 2850, 1755, 1710, 1675, 1505, 1085.
NMR(DMSO-d$_6$, ppm): 0.86(t, CH$_3$), 2.95(dd, J=3, 6 Hz, C$_4$—$\beta$H), 3.38(t, J=6 Hz, C$_4$—$\alpha$H), 3.4–4.1(m, —CH$_2$—), 4.87(ddd, J=3, 6, 8 Hz, C$_3$—H), 5.46(d, J=7Hz, —CH—),
|

7.2–7.5(m, arom.H), 7.99(s, NH), 9.12(d, J=8 Hz, NH), 9.81(d, J=7 Hz, NH).

(3)
(a) 3-[D-2-(4-n-amyl-2,3-dioxo-1-piperazinecarboxamido)-2-phenylacetamido]-2-oxoazetidine
(b) A
(c) IR$\nu_{max}^{KBr}$cm$^{-1}$: 3280, 1755, 1710, 1675, 1510.
NMR(DMSO-d$_6$, ppm): 0.87(t, CH$_3$), 2.95(dd, J=3, 6 Hz, C$_4$—$\beta$H), 3.39(t, J=6 Hz, C$_4$—$\alpha$H), 3.4–4.1(m, —CH$_2$—), 4.88(ddd, J=3, 6, 8 Hz, C$_3$—H), 5.46(d, J=7Hz, —CH—),
|

7.2–7.5(m, arom.H), 8.00(s, NH), 9.12(d, J=8 Hz, NH), 9.82(d, J=7 Hz, NH).

(4)
(a) 3-[D-2-(4-n-amyl-2,3-dioxo-1-piperazinecarboxamido)-2-thienylacetamido]-2-oxoazetidine
(b) A
(c) IR$\nu_{max}^{KBr}$cm$^{-1}$: 3280, 1755, 1710, 1675, 1505.
NMR(DMSO-d$_6$, ppm): 0.87(t, CH$_3$), 3.01(dd, J=3, 6 Hz, C$_4$—$\beta$H), 3.42(t, J=6 Hz, C$_4$—$\alpha$H), 3.4–4.1(m, —CH$_2$—), 4.88(ddd, J=3, 6, 8 Hz, C$_3$—H), 5.73(d, J=7Hz, —CH—),
|

6.9–7.3(m, arom.H), 8.01(s, NH), 9.16(d, J=8 Hz, NH), 9.74(d, J=7 Hz, NH).

(5)
(a) 3-[2-(5-chloro-2-chloroacetamidothiazol-4-yl)-2-methoxyiminoacetamido]-2-oxoazetidine
(b) B
(c) IR$\nu_{max}^{KBr}$cm$^{-1}$: 3260, 1740, 1665, 1555, 1040.

NMR(DMSO-d$_6$, ppm): 3.08(dd, J=3, 6 Hz, C$_4$—βH), 3.49(t, J=6 Hz, C$_4$—αH), 3.94(s, OCH$_3$), 4.39(s, —CH$_2$—), 5.00(ddd, J=3, 6, 8 Hz, C$_3$—H), 8.02(s, NH), 9.23(d, J=8 Hz, NH), 13.0(broad s, NH).

(6)
(a) 3-[D-2-(4,6(R)-diethyl-2,3-dioxo-1-piperazinecarboxamido)-2-phenylacetamido]-2-oxoazetidine
(b) A
(c) IRν$_{max}^{KBr}$cm$^{-1}$: 3270, 1750, 1705, 1670, 1500, 1090.

NMR(DMSO-d$_6$, ppm): 0.89(t, J=7 Hz, CH$_3$), 1.09(t, J=7 Hz, CH$_3$), 1.58(quintet, J=7 Hz, —CH$_2$—), 2.94(dd, J=3, 6 Hz, C$_4$—βH), 3.38(t, J=6 Hz, C$_4$—αH), 4.87(ddd, J=3, 6, 8 Hz, C$_3$—H), 5.41(d, J=7Hz, —CH—),
|

7.2–7.5(m, arom.H), 7.97(s, NH), 9.08(d, J=8 Hz, NH), 9.85(d, J=7 Hz, NH).

(7)
(a) 3-[D-2-(4,6(S)-diethyl-2,3-dioxo-1-piperazinecarboxamido)-2-phenylacetamido]-2-oxoazetidine
(b) A
(c) IRν$_{max}^{KBr}$cm$^{-1}$: 3270, 1750, 1705, 1670, 1500, 1090.

NMR(DMSO-d$_6$, ppm): 0.81(t, J=7 Hz, CH$_3$), 1.10(t, J=7 Hz, CH$_3$), 1.3–1.7(m, —CH$_2$—), 2.95(dd, J=3, 6 Hz, C$_4$—βH), 3.39(t, J=6 Hz, C$_4$—αH), 4.87(ddd, J=3, 6, 8 Hz, C$_3$—H), 5.41(d, J=7Hz, —CH—),
|

7.2–7.3(m, arom. H), 7.99(s, NH), 9.14(d, J=8 Hz, NH), 9.84(d, J=7 Hz, NH).

(8)
(a) 3-(2-phenyl-2-p-tolylthioiminoacetamido-2-oxoazetidine
(b) A
(c) IRν$_{max}^{KBr}$cm$^{-1}$: 3250, 1755, 1725, 1645.
NMR(DMSO-d$_6$, ppm): 2.33(s, CH$_3$), 3.28(dd, J=3, 6 Hz, C$_4$—βH), 3.55(t, J=6 Hz, C$_4$—αH), 4.8–5.2(m, C$_3$—H), 7.2–7.8(m, arom.H), 7.96, 8.06(each s, NH), 8.88(d, J=8 Hz, NH), 9.46(d, J=8 Hz, NH).

(9)
(a) 3-[D-2-(4-cyclohexyl-2,3-dioxo-1-piperazinecarboxamido)-2-phenylacetamido]-2-oxoazetidine
(b) A
(c) IRν$_{max}^{KBr}$cm$^{-1}$: 3280, 2930, 1755, 1710, 1670, 1505, 1180.

NMR(DMSO-d$_6$, ppm): 2.94(dd, J=3, 6 Hz, C$_4$—βH), 3.38(t, J=6 Hz, C$_4$—αH), 3.4–3.9(m, —CH$_2$—), 4.86(ddd, J=3, 6, 8 Hz, C$_3$—H), 5.44(d, J=7Hz, —CH—),
|

7.2–7.5(m, arom.H), 7.97(s, NH), 9.09(d, J=8 Hz, NH), 9.78(d, J=7 Hz, NH).

(10)
(a) 3-(2,6-dimethoxybenzamido)-2-oxoazetidine
(b) A
(c) KRν$_{max}^{KBr}$cm$^{-1}$: 3370, 1760, 1725, 1648, 1593, 1470, 1250, 1110.

NMR(DMSO-d$_6$, ppm): 3.08(dd, J=3, 6 Hz, C$_4$—H), 3.48(t, J=6 Hz, C$_4$—H), 3.76(s, CH$_3$), 5.01(ddd, J=3, 6, 9 Hz, C$_3$—H), 6.67(d, J=9 Hz, arom.H), 7.30(t, J=9 Hz, arom.H), 7.91(s, NH), 8.62(d, J=9 Hz, NH).

(11)
(a) 3-[D-2-(4-n-amyl-6(R)-methyl-2,3-dioxo-1-piperazinecarboxamido)-2-thienylacetamido]-2-oxoazetidine
(b) A
(c) IRν$_{max}^{KBr}$cm$^{-1}$: 3280, 1762, 1710, 1680, 1500, 1192.

NMR(DMSO-d$_6$, ppm): 0.88(t, J=7 Hz, CH$_3$), 1.25(d, J=6 Hz, CH$_3$), 3.01(dd, J=6 Hz, C$_4$—H), 3.41(t, J=6 Hz, C$_4$—H), 4.66(m, —CH—),
|

4.88(ddd, J=2, 6, 8 Hz, C$_3$—H), 5.69(d, J=7Hz, —CH—),
|
N 6.9–7.2(m, arom.H), 7.42(m, arom.H), 9.15(d, J=8 Hz, NH), 9.80(d, J=7 Hz, NH).

(12)
(a) 3-[D-2-(4-n-amyl-6(S)-methyl-2,3-dioxo-1-piperazinecarboxamido)-2-thienylacetamido]-2-oxoazetidine
(b) A
(c) IRν$_{max}^{KBr}$cm$^{-1}$: 3275, 1760, 1710, 1670, 1500, 1190.

NMR(DMSO-d$_6$, ppm): 0.88(t, J=7 Hz, CH$_3$), 1.22(d, J=6 Hz, CH$_3$), 3.03(dd, J=2, 6 Hz, C$_4$—H), 3.41(t, J=6 Hz, C$_4$—H), 4.68(m, —CH—),
|

4.88(ddd, J=2, 6, 8 Hz, C$_3$—H), 5.72(d, J=7Hz, —CH—),
|
N 6.9–7.2(m, arom.H), 7.43(m, arom.H), 9.21(d, J=8 Hz, NH), 9.80(d, J=7 Hz, NH).

(13)
(a) 3-[D-2-(4-n-amyl-6-methyl-2,3-dioxo-1-piperazinecarboxamido)-3-chloropropionamido]-2-oxoazetidine
(b) A
(c) IRν$_{max}^{KBr}$cm$^{-1}$: 3300, 1750, 1713, 1675, 1510, 1200.

NMR(DMSO-d$_6$, ppm): 0.88(t, J=6 Hz, CH$_3$), 1.24(d, J=6 Hz, CH$_3$), 2.80(dd, J=2, 6 Hz, C$_4$—H), 4.28(m, —CH—), 4.65(m, —CH—),
|                |

4.86(m, C$_3$—H), 7.96(broad s, NH), 8.72(d, J=8 Hz, NH), 9.35(d, J=7 Hz, NH).

(14)

(a) 3-[D-2-[[3-(2,6-dichlorophenyl)-5-methylisoxazol-4-yl]carboxamido]-2-thienylacetamido]-2-oxoazetidine
(b) A
(c) IR$\nu_{max}^{KBr}$cm$^{-1}$: 3270, 1755, 1653.

NMR(DMSO-d$_6$, ppm): 2.71(s, CH$_3$), 2.96(dd, J=3, 6 Hz, C$_4$—H), 3.37(t, J=6 Hz, C$_4$—H), 4.80(m, C$_3$—H), 5.70(d, J=8Hz, —CH—),
|

6.97(m, arom.H), 7.39(m, arom.H), 7.55(s, arom.H), 7.94(d, J=7 Hz, NH), 7.91(broad s, NH), 9.01(d, J=8 Hz, NH).

(15)
(a) 3-[D-2-(4-ethyl-5(R)-methyl-2,3-dioxo-1-piperazinecarboxamido)-2-thienylacetamido]-2-oxoazetidine
(b) A
(c) IR$\nu_{max}^{KBr}$cm$^{-1}$: 3270, 1755, 1702, 1665, 1500, 1180.

NMR(DMSO-d$_6$, ppm): 1.14(t, J=7 Hz, CH$_3$), 1.20(d, J=7 Hz, CH$_3$), 3.02(dd, J=3, 6 Hz, C$_4$—H), 3.43(t, J=6 Hz, C$_4$—H), 4.88(m, C$_3$—H), 5.73(d, J=7Hz, —CH—),
|

8.01(s, NH), 9.18(d, J=8 Hz, NH), 9.72(d, J=7 Hz, NH).

(16)
(a) 3-[D-2-(4-ethyl-5(S)-methyl-2,3-dioxo-1-piperazinecarboxamido)-2-thienylacetamido]-2-oxoazetidine
(b) A
(c) IR$\nu_{max}^{KBr}$cm$^{-1}$: 3270, 1755, 1705, 1665, 1500, 1180.

NMR(DMSO-d$_6$, ppm): 1.12(t, J=7 Hz, CH$_3$), 1.22(d, J=6 Hz, CH$_3$), 3.00(dd, J=3, 6 Hz, C$_4$—H), 3.42(t, J=6 Hz, C$_4$—H), 4.90(m, C$_3$—H), 5.70(d, J=7Hz, —CH—),
|

6.9-7.2(m, arom. H), 7.4-7.5(m, arom.H), 8.00(s, NH), 9.16(d, J=8 Hz, NH), 9.70(d, J=7 Hz, NH).

(17)
(a) 3-[D-2-[(2-oxoimidazolidin--yl)carboxamido]-2-thienylacetamido]-2-oxoazetidine
(b) A
(c) IR$\nu_{max}^{KBr}$cm$^{-1}$: 3270, 1750, 1725, 1658.

NMR(DMSO-d$_6$, ppm): 2.90-4.00(m, —CH$_2$—, C$_4$—H), 4.83(m, C$_3$—H), 5.68(d, J=8Hz, —CH—),
|

7.10-7.37(m, arom.H), 7.45(s, NH), 7.87(s, NH), 9.00(d, J=8 Hz, NH),

(18)
(a) 3-[D-2-[(5-methoxycarbonyl-3-methyl-2-oxoimidazolidin-1-yl)carboxamido]-2-phenylacetamido]-2-oxoazetidine
(b) A
(c) IR$\nu_{max}^{KBr}$cm$^{-1}$: 3280, 1750, 1720, 1660.

NMR(DMSO-d$_6$, ppm): 2.76(s, CH$_3$), 2.95(dd, J=3, 6Hz, C$_4$—H), 3.34(dd, J=4, 10 Hz, —CH$_2$—), 3.38(t, J=6 Hz, C$_4$—H), 3.69(s, OCH$_3$), 4.66(dd, J=4, 10Hz, —CH—),
|

4.85(m, C$_3$—H), 5.40(d, J=8Hz, —CH—),
|

7.33(s, arom.H), 7.98(s, NH), 9.07(d, J=8 Hz, NH), 9.11(d, J=8 Hz, NH).

(19)
(a) 3-[D-2-[(5-benzyloxycarbonyl-3-methyl-2-oxoimidazolidin-1-yl)carboxamido]-2-phenylacetamido]-2-oxoazetidine
(b) A
(c) IR$\nu_{max}^{KBr}$cm$^{-1}$: 3310, 1750, 1740, 1712, 1688, 1660.

NMR(DMSO-d$_6$, ppm): 2.74(s, CH$_3$), 2.92(dd, J=3, 5 Hz, C$_4$—H), 3.20-3.47(m, C$_4$—H, —CH$_2$—), 3.68(t, J=10 Hz, —CH$_2$—, 4.65(dd, J=4, 10Hz, —CH—),
|

4.83(m, C$_3$—H), 5.15(s, —CH$_2$—, 5.39(d, J=8Hz, —CH—),
|

7.34(s, arom.H), 7.96(s, NH), 9.08(d, J=8 Hz, NH), 9.12(d, J=8 Hz, NH).

(20)
(a) 3-[2-(4-ethyl-2,3-dioxo-1-piperazinecarboxamido)-2-(2-chloro-1-cyclohexene-1-yl)acetamido]-2-oxoazetidine
(b) A
(c) IR$\nu_{max}^{KBr}$cm$^{-1}$: 1760, 1715, 1670, 1510.

(21)
(a) 3-[2-(2-tritylaminothiazol-4-yl)-2-[(1-t-buthoxycarbonyl-1-methyl)ethoxyimino]acetamido]-2-oxoazetidine
(b) A
(c) IR$\nu_{max}^{KBr}$cm$^{-1}$: 1760, 1725, 1675, 1520, 1140.

NMR(DMSO-d$_6$, ppm): 1.33(s, CH$_3$), 3.03(dd, J=2, 6 Hz, C$_4$—$\beta$H), 3.20(s, CH$_2$—), 3.36(t, J=6 Hz, C$_4$—$\alpha$H), 4.86(m, C$_3$—H), 6.66 (s, ⋎H),
||

7.15-7.40(m, arom.H), 7.90(broad s, NH), 8.66(s, NH), 8.70(d, J=8 Hz, NH).

(22)
(a) 3-[2-(2-chloroacetamidothiazol-4-yl)-2-(1-methylethoxyimino)acetamido]-2-oxoazetidine
(b) A
(c) IR$\nu_{max}^{KBr}$cm$^{-1}$: 3250, 1750, 1655, 1540.
NMR(DMSO-d$_6$, ppm):

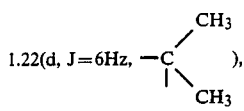

3.13(dd, J=2, 6 Hz, C$_4$—βH), 3.46(t, J=6 Hz, C$_4$—αH),

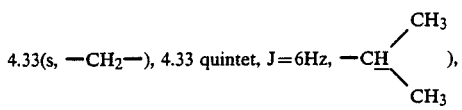

8.0(broad s, NH), 9.10(d, J=8 Hz, NH).

(23)
(a) 3-(2-oxo-2-phenylacetamido)-2-oxoazetidine
(b) B
(c) IR$\nu_{max}^{KBr}$cm$^{-1}$: 3280, 1745, 1720, 1660.
NMR(DMSO-d$_6$, ppm): 3.31(dd, J=3, 5 Hz, C$_4$—H), 3.49(t, J=5 Hz, C$_4$—H) 5.00(ddd, J=3, 5, 8 Hz, C$_3$—H), 7.45–8.20(m, arom.H), 8.01(s, NH), 9.55(d, J=8 Hz, NH).

(24)
(a) 3-[2-(2-mesylaminothiazol-4-yl)-2-(1-methylethoxyimino)acetamido]-2-oxoazetidine
(b) B
(c) IR$\nu_{max}^{KBr}$cm$^{-1}$: 3275, 1750, 1660, 1535, 1120.
NMR(DMSO-d$_6$, ppm):

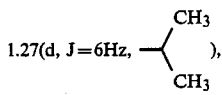

2.96(s, CH$_3$), 3.14(dd, J=3, 5 Hz, C$_4$—H), 3.48(t, J=5 Hz, C$_4$—H), 4.36(heptet, J=6Hz, —CH—), 4.95(m, C$_3$—H),

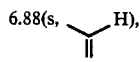

8.01(s, NH), 9.20(d, J=8 Hz, NH).

(25)
(a) 3-(2-bromo-2-phenylacetamido)-2-oxoazetidine
(b) A
(c) IR$\nu_{max}^{KBr}$cm$^{-1}$: 3280, 1755, 1730, 1660.
NMR(DMSO-d$_6$, ppm): 3.03–3.73(m, C$_4$—H), 3.47, 3.52(each t, J=5 Hz, C$_4$—H), 4.94(m, C$_3$—H),

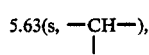

7.30–7.90(m, arom.H), 8.07(s, NH), 9.28(d, J=9 Hz, NH).

(26)
(a) 3-(2-azido-2-phenylacetamido)-2-oxoazetidine
(b) A
(c) IR$\nu_{max}^{KBr}$cm$^{-1}$: 3300, 2103, 1752, 1670.
NMR(DMSO-d$_6$, ppm): 3.47(t, J=6 Hz, C$_4$—H), 3.50(t, J=6 Hz, C$_4$—H), 5.00(m, C$_3$—H), 5.09(s, —CH—), 7.52(s, arom.H), 8.07(broad s, NH), 9.12(d, J=8 Hz, NH).

(27)
(a) 3-tosylamino-2-oxoazetidine
(b) B
(c) IR$\nu_{max}^{KBr}$cm$^{-1}$: 3265, 3080, 1745, 1330, 1155.
NMR(DMSO-d$_6$, ppm): 2.49(s, CH$_3$), 2.98(dd, J=3, 5 Hz, C$_4$—H), 3.30(t, J=5 Hz, C$_4$—H), 4.60(m, C$_3$—H),

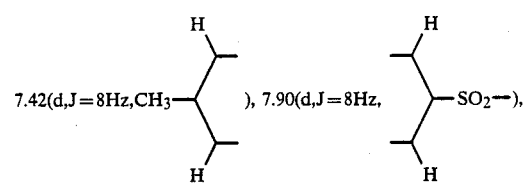

8.26(d, J=8 Hz, NH).

(28)
(a) 3-(2-phthalimido-2-thienylacetamido)-2-oxoazetidine
(b) A
(c) IR$\nu_{max}^{KBr}$cm$^{-1}$: 3280, 1760, 1710, 1660, 1520, 1380, 1100, 720.
NMR(DMSO-d$_6$, ppm): 2.99, 3.20(each dd, J=4, 2 Hz, C$_4$—βH), 3.40, 3.43(each t, J=4 Hz, C$_4$—αH), 4.70–5.15(m, C$_3$—H), 6.20,

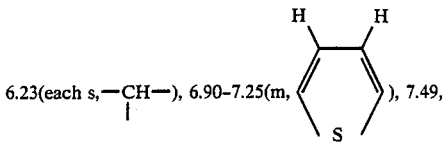

7.97, 8.00(s, arom.H), 8.83, 8.93(each d, J=6 Hz, NH).

(29)
(a) 3-[2-azido-2-(3-chlorophenyl)acetamido]-2-oxoazetidine
(b) A
(c) IR$\nu_{max}^{KBr}$cm$^{-1}$: 3250, 2100, 1750, 1660.
NMR(DMSO-d$_6$, ppm): 3.20–3.70(m, C$_4$—H), 5.08(s, —CH—), 4.90–5.20(m, C$_3$—H), 6.93(s, NH), 7.40(s, arom.H), 8.03(m, NH).

(30)
(a) 3-(2-azido-2-phenylacetamido)-3-methoxy-2-oxoazetidine
(b) B
(c) IR$\nu_{max}^{KBr}$cm$^{-1}$: 3260, 2100, 1755, 1682.

NMR(DMSO-d₆, ppm): 3.36, 3.43(each s, CH₃), 3.75(dd, J=6 Hz, C₄—H), 5.15(s,—CH—),
|

6.95(s, NH), 7.50(s, arom.H), 8.08(s, NH).

(31)
(a) 3-[D-2-(4-cyclohexyl-2,3-dioxo-1-piperadinecarboxamido)-2-thienylacetamido]-2-oxoazetidine
(b) A
(c) IR$\nu_{max}^{KBr}$cm⁻¹: 3280, 2930, 1755, 1710, 1670, 1505, 1190
NMR(DMSO-d₆, ppm): 3.01(dd, J=3, 6 Hz, C₄—βH), 3.42(t, J=6 Hz, C₄—αH), 4.87(ddd, J=3, 6, 8 Hz, C₃—H), 5.72(d,J=7Hz,—CH—),
|

6.9-7.5(m, arom.H), 7.99(s, NH), 9.15(d, J=8 Hz, NH), 9.73(d, J=7 Hz, NH).

(32)
(a) 3-[2-(2-aminothiazol-4-yl)-2-(1-methylethoxyimino)acetamido]-3-methoxy-2-oxoazetidine
(b) B
(c) IR$\nu_{max}^{KBr}$cm⁻¹: 1735, 1690, 1665, 1540, 1255.
NMR(DMSO-d₆, ppm): 0.28, 0.30(each s, Si(CH₃)₂), 1.00(s, Si-t-Bu), 1.15,

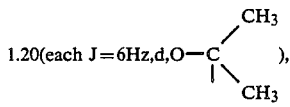
1.20(each J=6Hz,d,O—C(CH₃)(CH₃)), 3.57(s, OCH₃), 3.70(d, J=7 Hz, C₄—H), 3.95(d, J=7 Hz, C₄—H), 4.25(s, —CH₂—), 4.28(quintet J=6 Hz, —CH<),

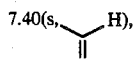
7.40(s, ⟨H⟩), 8.00(broad s, NH), 10.66(broad s, NH)

(33)
(a) 3-[2-(2-mesylaminothiazol-4-yl)-2-(1-methylethoxyimino)acetamido]-3-methoxy-2-oxoazetidine
(b) B
(c) IR$\nu_{max}^{KBr}$cm⁻¹: 3250, 1760, 1672, 1535, 1120.
NMR(DMSO-d₆, ppm): 1.25(d, J=6 Hz, CH₃), 2.94(s, CH₃), 3.41(s, CH₃),

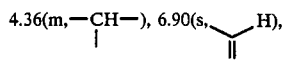
4.36(m,—CH—), 6.90(s, ⟨H⟩),
|

8.34(s, NH).

(34)
(a) 3-[D-2-(4-cyclohexyl-2,3-dioxo-1-piperadinecarboxamido)-2-thienylacetamido]-3-methoxy-2-oxoazetidine
(b) B
(c) IR$\nu_{max}^{KBr}$cm⁻¹: 2920, 1760, 1705, 1670, 1500, 1170.
NMR(DMSO-d₆, ppm): 3.18(s, CH₃), 3.48(ABq, J=6, 12 Hz, C₄—H), 5.87(d,J=7Hz,—CH—),
|

6.9-7.6(m, arom. H), 8.34(s, NH), 9.66(s, NH), 9.71(d, J=7 Hz, NH).

(35)
(a) 3-methoxy-3-[D-2-(4-piperidinecarbonyl-2,3-dioxo-1-piperadinecarboxamido)-2-thienylacetamido]-2-oxoazetidine
(b) B
(c) IR$\nu_{max}^{KBr}$cm⁻¹: 3280, 2930, 1760, 1705, 1680, 1640.
NMR(DMSO-d₆, ppm): 3.20(s, CH₃), 4.32(s, —CH₂—), 5.89(d,J=7Hz,—CH—),
|

6.9-7.6(m, arom.H), 8.36(s, NH), 9.69(s, NH), 9.72(d, J=7 Hz, NH).

(36)
(a) 3-methoxy-3-[D-2-(4-phenyl-2,3-dioxo-1-piperadinecarboxamido)-2-thienylacetamido]-2-oxoazetidine
(b) B
(c) IR$\nu_{max}^{KBr}$cm⁻¹: 3275, 1760, 1705, 1680, 1490, 1200.
NMR(DMSO-d₆, ppm): 3.21(s, CH₃), 3.44, 3.57(each d, J=6 Hz, C₄—H), 5.92(d,J=7Hz,—CH—),
|

6.9-7.6(m, arom.H), 8.36(s, NH), 9.70(s, NH), 9.78(d, J=7 Hz, NH).

(37)
(a) 3-[D-2-(4-t-butyl-2,3-dioxo-1-piperadinecarboxamido)-2-thienylacetamido]-3-methoxy-2-oxoazetidine
(b) B
(c) IR$\nu_{max}^{KBr}$cm⁻¹: 3280, 2970, 1760, 1710, 1675, 1505, 1200.
NMR(DMSO-d₆, ppm): 1.4(s, CH₃), 3.43, 3.55(each d, J=6 Hz, C₄—H), 3.19(s, CH₃), 5.88(d,J=7Hz,—CH—),
|

6.9-7.6(m, arom.H), 8.36(s, NH), 9.67(d, J=7 Hz, NH), 9.67(s, NH).

(38)
(a) 3-[D-2-(4-(3-methyl-2-butenyl)-2,3-dioxo-1-piperadinecarboxamido)-2-thienylacetamido]-3-methoxy-2-oxoazetidine
(b) B
(c) IR$\nu_{max}^{KBr}$cm⁻¹: 3250, 1770, 1705, 1675, 1660, 1510, 1185.
NMR(DMSO-d₆, ppm): 1.70(d, J=3 Hz, CH₃), 3.19(s, CH₃), 3.43, 3.55(each d, J=6 Hz, C₄—H), 5.88(d,J=7Hz,—CH—),
|

6.9-7.6(m, arom.H), 8.35(s, NH), 9.67(s, NH), 9.73(d, J=7 Hz, NH).

(39)
(a) 3-[D-2-phenyl-2-[[3-(3-thienylidene)amino-2-oxoimidazolydin-1-yl]carboxamido]acetamido]-2-oxoazetidine
(b) A
(c) IR$\nu_{max}^{KBr}$cm$^{-1}$: 3280, 1750, 1710.

(40)
(a) 3-[2-[4-(tetrahydropyran-2-yloxy)phenyl]-2-(4-methoxyphenyloxycarbonyl)acetamido]-3-methoxy-2-oxoazetidine
(b) B
(c) IR$\nu_{max}^{KBr}$cm$^{-1}$: 1750, 1680, 1505, 1240.
NMR(DMSO-d$_6$, ppm): 1.4-1.9(m, —CH$_2$—), 3.14, 3.30(each s, CH$_3$), 3.76(s, CH$_3$), 4.87(s, —CH—), 5.06(s, —CH$_2$—), 5.43(broad s, —CH<), 8.33, 8.24(each s, NH), 9.41, 9.45 (each s, NH).

(41)
(a) 3-[2-[(1-carboxy-1-methylethoxy)imino]-2-(2-tritylaminothiazol-4-yl)acetamido]-2-oxoazetidine
(b) A
(c) IR$\nu_{max}^{KBr}$cm$^{-1}$: 1750, 1615, 1526.
NMR(DMSO-d$_6$, ppm): 1.34 (s, CH$_3$), 1.40 (s, CH$_3$), 3.05 (dd, J=3, 6 Hz, C$_4$—H), 3.18 (t, J=6 Hz, C$_4$—H), 4.73 (m, C$_3$—H),

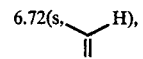

7.17-7.50 (m, arom. H), 7.83 (s, NH), 8.58 (s, NH), 9.58 (d, J=9 Hz, NH).

SYNTHESIS EXAMPLE 1

To a solution of 0.36 g of 3-[D-2-[(3-furfurylideneamino-2-oxoimidazolidin-1-yl)carboxamido]-proprionamido]-2-oxoazetidine in 2 ml of DMF is added 0.15 g of pyridinesulfuric anhydride complex, and the reaction is allowed to proceed at room temperature for 2 days. Diethyl ether is added to the reaction mixture, whereupon an oily substance separates. This is passed through a Dowex 50W Na-type resin (Dow Chemical) column and the eluate is purified with an Amberline XAD-II (Rohm and Haas, USA) column to give 0.37 g of sodium 3-[D-2-[(3-furfurylideneamino-2-oxoimidazolidin-1-yl)carboxamido]propionamido]-2-oxoazetidine-1-sulfonate.

IR$\nu_{max}^{KBr}$cm$^{-1}$: 3300, 1755, 1725, 1415, 1270, 1235, 1050.
NMR(DMSO-d$_6$, ppm): 1.29 (d, J=7 Hz, CH$_3$), 3.26 (dd, J=3, 6 Hz, C$_4$—βH), 3.68 (t, J=6 Hz, C$_4$—αH), 3.81 (s, —CH$_2$—), 4.33(quintet, J=7Hz, —CH—), 4.86 (ddd, J=3, 6, 8 Hz, C$_3$—H), 6.5-7.9 (m, furyl H), 7.74 (s, —CH=N—), 8.43 (d, J=7 Hz, NH), 8.87 (d, J=8 Hz, NH).

In substantially the same manner as in Synthesis Example 1, the following compounds are produced by sulfonation of the corresponding 2-oxoazetidine derivatives:

SYNTHESIS EXAMPLE 2

Sodium 3-[D-2-[(3-furfurylideneamino-2-oxoimidazolidin-1-yl)carboxamido]propionamido]-3(S)-methoxy-2-oxoazetidine-1-sulfonate IR$\nu_{max}^{KBr}$cm$^{-1}$: 1768, 1722, 1670, 1520, 1480, 1420, 1270, 1240, 1050.
NMR(DMSO-d$_6$, ppm): 1.32 (d, J=7 Hz, CH$_3$), 3.35 (s, OCH$_3$), 3.68 (q, J=7, 13 Hz, C$_4$—H), 3.80 (s, —CH$_2$—), 4.46(quintet, J=7Hz, —CH—), 6.5-7.9 (m, arom. H), 7.73 (s, —CH=N—), 8.43 (d, J=7 Hz, NH), 9.38 (s, NH).

Synthesis Example 3

Sodium 3-[D-2-[(3-furfurylideneamino-2-oxoimidazolidin-1-yl)carboxamido]propionamido]-3(R)-methoxy-2-oxoazetidine-1-sulfonate IR$\nu_{max}^{KBr}$cm$^{-1}$: 1768, 1722, 1670, 1520, 1480, 1420, 1270, 1240, 1050.
NMR(DMSO-d$_6$, ppm): 1.30 (d, J=7 Hz, CH$_3$), 3.34 (s, CH$_3$), 3.59 (q, J=6, 12 Hz, C$_4$—H), 3.80 (s, —CH$_2$—), 4.45(quintet, J=7Hz, —CH—), 6.5-7.9 (m, arom. H), 7.73 (s, —CH=N—), 8.42 (d, J=7 Hz, NH), 9.35 (s, NH).

SYNTHESIS EXAMPLE 4

Sodium 3-[D-2-(4-n-octyl-2,3-dioxo-1-piperazinecarboxamido)-2-thienylacetamido]-2-oxoazetidine-1-sulfoante IR$\nu_{max}^{KBr}$cm$^{-1}$: 3280, 2925, 2855, 1760, 1710, 1675, 1505, 1270-1240, 1190, 1050.
NMR(DMSO-d$_6$, ppm): 0.86 (t, J=7 Hz, CH$_3$), 1.1-1.7 (m, —CH$_2$—), 3.17 (dd, J=3, 6 Hz, C$_4$—βH), 3.3-4.1 (m, —CH$_2$—), 3.62 (t, J=6 Hz, C$_4$—αH), 4.87 (ddd, J=3, 6, 8 Hz, C$_3$—H), 5.72(d, J=7Hz, —CH—), 6.9-7.6 (m, arom. H), 9.30 (d, J=8 Hz, NH), 9.37 (d, J=7 Hz, NH).

SYNTHESIS EXAMPLE 5

Sodium 3-[D-2-(4-n-dodecyl-2,3-dioxo-1-piperazinecarboxamido)-2-phenylacetamido]-2-oxoazetidine-1-sulfonate IR$\nu_{max}^{KBr}$cm$^{-1}$: 3280, 2920, 2850, 1760, 1710, 1675, 1505, 1270-1240, 1190.
NMR(DMSO-D$_6$, ppm): 0.85 (t, J=7 Hz, CH$_3$), 3.11 (dd, J=3, 6 Hz, C$_4$—βH), 3.57 (t, J=6 Hz, C$_4$—αH), 4.85 (ddd, J=3, 6, 8 Hz, C$_3$—H), $$5.44(d, J=7Hz, -\underset{|}{CH}-),$$

7.2–7.5 (m, arom. H), 9.24 (d, J=8 Hz, NH), 9.79 (d, J=7 Hz, NH).

SYNTHESIS EXAMPLE 6

Sodium 3-[D-2-(4-n-amyl-2,3-dioxo-1-piperazinecarboxamido)-2-phenylacetamido]-2-oxoazetidine-1-sulfonate IR$\nu_{max}^{KBr}$cm$^{-1}$: 3290, 1760, 1710, 1675, 1510, 1280–1240, 1195, 1050.

NMR(DMSO-d$_6$, ppm): 0.87 (t, CH$_3$), 3.13 (dd, J=3, 6 Hz, C$_4$—$\beta$H), 3.4–4.1 (m, —CH$_2$—), 3.58 (t, J=6 Hz, C$_4$—$\alpha$H), 4.85 (ddd, J=3, 6, 8 Hz, C$_3$—H), $$5.44(d, J=7Hz, -\underset{|}{CH}-),$$

7.2–7.5 (m, arom. H), 9.25 (d, J=8 Hz, NH), 9.80 (d, J=7 Hz, NH).

SYNTHESIS EXAMPLE 7

Sodium 3-[D-2-(4-n-amyl-2,3-dioxo-1-piperazinecarboxamido)-2-thienylacetamido]-2-oxoazetidine-1-sulfonate IR$\nu_{max}^{KBr}$cm$^{-1}$: 3280, 1760, 1710, 1675, 1505, 1280–1230, 1195, 1050.

NMR(DMSO-d$_6$, ppm): 0.87 (t, J=7 Hz, CH$_3$), 3.19 (dd, J=3, 6 Hz, C$_4$—$\beta$H), 3.63 (t, J=6 Hz, C$_4$—$\alpha$H), 3.4–4.1 (m, —CH$_2$—), 4.88 (ddd, J=3, 6, 8 Hz, C$_3$—H), $$5.74(d, J=7Hz, -\underset{|}{CH}-),$$

6.9–7.6 (m, arom. H), 9.30 (d, J=8 Hz, NH), 9.74 (d, J=7 Hz, NH).

SYNTHESIS EXAMPLE 8

Sodium 3-[2-(5-chloro-2-chloroacetamidothiazol-4-yl)-2-methoxyiminoacetamido]-2-oxoazetidine-1-sulfonate IR$\nu_{max}^{KBr}$cm$^{-}$: 1760, 1665, 1540, 1270, 1240, 1050.

NMR(DMSO-d$_6$, ppm): 3.32 (dd, J=3, 6 Hz, C$_4$—$\beta$H), 3.68 (t, J=6 Hz, C$_4$—$\alpha$H), 3.94 (s, OCH$_3$), 4.40 (s, ClCH$_2$—), 4.95 (ddd, J=3, 6, 8 Hz, C$_3$—H), 9.36 (d, J=8 Hz, NH).

The above compound is reacted, in an aqueous solution, with sodium monomethyldithiocarbamate and the product is purified with an XAD-II column to give sodium 3-[2-(2-amino-5-chlorothiazol-4-yl)-2-methoxyiminoacetamido]-2-oxoazetidine-1-sulfonate.

IR$\nu_{max}^{KBr}$cm$^{-1}$: 1755, 1650, 1625, 1530, 1270, 1240, 1050.

NMR(DMSO-d$_6$, ppm): 3.26 (dd, J=3, 6 Hz, C$_4$—$\oplus$H), 3.65 (t, J=6 Hz, C$_4$—$\alpha$H), 3.89 (s, OCH$_3$), 4.91 (ddd, J=3, 6, 8 Hz, C$_3$—H), 9.23 (d, J=8 Hz, NH).

SYNTHESIS EXAMPLE 9

Sodium 3-[D-2-(4,6(R)-diethyl-2,3-dioxo-1-piperazinecarboxamido)-2-phenylacetamido]-2-oxoazetidine-1-sulfonate IR$\nu_{max}^{KBr}$cm$^{-1}$: 3280, 1760, 1710, 1675, 1500, 1270, 1240, 1190, 1050.

NMR(DMSO-d$_6$, ppm): 0.89 (t, J=7 Hz, CH$_3$), 1.09 (t, J=7 Hz, CH$_3$), 1.58 (quintet, J=7 Hz, —CH$_2$—), 3.10 (dd, J=3, 6 Hz, C$_4$—$\beta$H), 3.57 (t, J=6 Hz, C$_4$—$\alpha$H), 4.85 (ddd, J=3, 6, 8 Hz, C$_3$—H), $$5.40(d, J=7Hz, -\underset{|}{CH}-),$$

7.2–7.5 (m, arom. H), 9.21 (d, J=8 Hz, NH), 9.83 (d, J=7 Hz, NH).

SYNTHESIS EXAMPLE 10

Sodium 3-[D-2-(4,6(S)-diethyl-2,3-dioxo-1-piperazinecarboxamido)-2-pheylacetamido]-2-oxoazetidine-1-sulfonate IR$\nu_{max}^{KBr}$cm$^{-1}$: 3280, 1760, 1710, 1675, 1500, 1270, 1240, 1190, 1050.

NMR(DMSO-d$_6$, ppm): 0.81 (t, J=8 Hz, CH$_3$), 1.10 (t, J=7 Hz, CH$_3$), 1.3–1.7 (m, —CH$_2$—), 3.13 (dd, J=3, 6 Hz, C$_4$—$\beta$H), 3.58 (t, J=7 Hz, C$_4$—$\alpha$H), 4.85 (ddd, J=3, 6, 8 Hz, C$_3$—H), $$5.45(d, J=7Hz, -\underset{|}{CH}-),$$

7.2–7.5 (m, arom. H), 9.25 (d, J=8 Hz, NH), 9.83 (d, J=7 Hz, NH).

SYNTHESIS EXAMPLE 11

Sodium 3-(2-phenyl-2-p-tolylthioiminoacetamido)-2-oxoazetidine-1-sulfonate

IR$\nu_{max}^{KBr}$cm$^{-1}$: 1760, 1655, 1505, 1265, 1240, 1050.

NMR(DMSO-d$_6$, ppm): 2.34 (s, CH$_3$), 3.3–3.6 (m, C$_4$$\beta$H), 3.70, 3.75 (t, J=6 Hz, C$_4$—$\alpha$H), 4.8–5.2 (m, C$_3$—H), 7.2–7.8 (m, arom. H), 9.02, 9.59 (d, J=8 Hz, NH).

SYNTHESIS EXAMPLE 12

Sodium 3-[D-2-(4-cyclohexyl-2,3-dioxo-1-piperazinecarboxamido)-2-phenylacetamido]-2-oxoazetidine-1-sulfonate IR$\nu_{max}^{KBr}$cm$^{-1}$: 2925, 1760, 1705, 1665, 1505, 1250, 1180, 1045.

NMR(DMSO-d$_6$, ppm): 3.11 (dd, J=3, 6 Hz, C$_4$—$\beta$H), 3.4–4.0 (m, —CH$_2$—), 3.57 (t, J=6 Hz, C$_4$—$\alpha$H), 4.83 (ddd, J=3, 6, 8 Hz, C$_3$—H), $$5.42(d, J=7Hz, -\underset{|}{CH}-),$$

7.2–7.5 (m, arom. H), 9.22 (d, J=8 Hz, NH), 9.77 (d, J=7 Hz, NH).

SYNTHESIS EXAMPLE 13

Sodium 3-(2,6-dimethoxybenzamido)-2-oxoazetidine-1-sulfonate

IR$\nu_{max}^{KBr}$cm$^{-1}$: 3300, 1755, 1648, 1595, 1513, 1470, 1250, 1100, 1050.

NMR(DMSO-d$_6$, ppm): 3.27 (dd, J=3, 6 Hz, C$_4$—H), 3.62 (t, J=6 Hz, C$_4$—H), 3.71 (s, OCH$_3$), 4.93 (ddd, J=3, 6, 8 Hz, C$_3$—H), 6.60 (d, J=9 Hz, arom. H), 7.24 (t, J=9 Hz, arom. H), 8.71 (d, J=8 Hz, NH).

SYNTHESIS EXAMPLE 14

Sodium 3-[D-2-(4-n-amyl-6(R)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1760, 1710, 1678, 1503, 1272, 1240, 1198, 1050.

NMR(DMSO-d$_6$, ppm): 0.88 (t, J=7 Hz, CH$_3$), 1.25 (d, J=6 Hz, CH$_3$), 3.19 (dd, J=2, 6 Hz, C$_4$—H), 3.63 (t, J=6 Hz, C$_4$—H), 4.67(m,—CH—), 4.89(ddd,J=2,6,7Hz,C$_3$—H),
         |

5.70(d,J=8Hz,—CH—),
              |
              N 6.94–7.16 (m, arom. H), 7.42–7.54 (m, arom. H), 9.78 (d, J=7 Hz, NH).

SYNTHESIS EXAMPLE 15

Sodium 3-[D-2-(4-n-amyl-6(S)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1760, 1710, 1678, 1503, 1272, 1240, 1198, 1050.

NMR(DMSO-d$_6$, ppm): 0.87 (t, J=7 Hz, CH$_3$), 1.21 (d, J=6 Hz, CH$_3$), 3.19 (dd, J=2, 6 Hz, C$_4$—H), 3.61 (t, J=6 Hz, C$_4$—H), 4.66(m,—CH—), 4.87(dd,J=2,6,7Hz,C$_3$—H),
         |

5.73(d,J=8Hz,—CH—),
              |
              N 6.92–7.16 (m, arom. H), 7.42–7.53 (m, arom. H), 9.76 (d, J=7 Hz, NH)

SYNTHESIS EXAMPLE 16

Sodium 3-[D-2-(4-n-amyl-6-methyl-2,3-dioxo-1-piperazinecarboxamido)-3-chloropropionamido]-2-oxoazetidine-1-sulfonate IR$\nu_{max}^{KBr}$cm$^{-}$: 1760, 1712, 1680, 1520, 1240, 1055, 1010.

NMR(DMSO-d$_6$, ppm): 0.88 (t, J=6 Hz, CH$_3$), 1.24 (d, J=6 Hz, CH$_3$), 3.60 (t, J=6 Hz, C$_4$—H), 4.0 (broad s, —CH$_2$—), 4.48 (m, C$_3$—H), 8.90 (d, J=8 Hz, NH), 9.28 (d, J=7 Hz, NH).

SYNTHESIS EXAMPLE 17

Sodium 3-[D-2-[[3-(2,6-dichlorophenyl)-5-methylisoxazol-4-yl]-carboxamido]-2-thienylacetamido]-2-oxoazetidine-1-suflonate IR$\nu_{max}^{KBr}$cm$^{-1}$: 1760, 1665, 1603, 1508, 1271, 1240, 1200, 1050.

NMR(DMSO-d$_6$, ppm): 2.71 (s, CH$_3$), 3.16 (dd, J=3, 6 Hz, C$_4$—H), 3.60 (t, J=6 Hz, C$_4$—H), 4.81 (m, C$_3$—H), 5.70(d, J=7Hz, —CH—),
             |

6.93 (m, arom. H), 7.38 (m, arom. H), 7.59 (s, arom. H), 7.93 (d, J=7 Hz, NH), 9.14 (d, J=8 Hz, NH).

SYNTHESIS EXAMPLE 18

Sodium 3-[D-2-(4-ethyl-5(R)-methyl-2,3-dioxo-1-piperazinecarboxamido)-2-thienylacetamido]-2-oxoazetidine-1-sulfonate IR$_{max}^{KBr}$cm$^{-1}$: 3275, 1759, 1703, 1667, 1505, 1275, 1240, 1190.

NMR(DMSO-d$_6$, ppm): 1.13 (t, J=7 Hz, CH$_3$), 3.18 (dd, J=3, 6 Hz, C$_4$—H), 4.87 (m, C$_4$—H), 5.72(d,J=7Hz,—CH—),
             |

9.28 (d, J=8 Hz, NH), 9.70 (d, J=7 Hz, NH).

SYNTHESIS EXAMPLE 19

Sodium 3-[D-2-(4-ethyl-5(S)-methyl-2,3-dioxo-2,3-dioxo-1-piperazinecarboxamido)-2-thienylacetamido]-2-oxoazetidine-1-sulfonate IR$\nu_{max}^{KBr}$cm$^{-1}$: 3275, 1759, 1703, 1667, 1505, 1275, 1240, 1190.

NMR(DMSO-d$_6$, ppm): 1.18 (t, J=7 Hz, CH$_3$), 1.24 (t, J=6 Hz, CH$_3$), 3.19 (dd, J=3, 6 Hz, C$_4$—H), 3.62 (t, J=6 Hz, C$_4$—H), 4.88 (m, C$_3$—H), 5.69(d,J=7Hz,—CH—),
             |

9.29 (d, J=8 Hz, NH), 9.69 (d, J=7 Hz, NH).

SYNTHESIS EXAMPLE 20

Disodium 3-[D-2-[(2-oxo-3-sulfonatoimidazolindin-1-yl)carboxamido]-2-thienylacetamido]-2-oxoazetidine-1-sulfonate IR$\nu_{max}^{KBr}$cm$^{-1}$: 3470, 3300, 1755, 1710, 1668, 1260, 1052.

NMR(DMSO-d$_6$, ppm): 3.25 (dd, J=3, 6 Hz, C$_4$—H), 3.52 (t, J=6 Hz, C$_4$—H), 3.61 (s, —CH$_2$—), 4.83 (m, C$_3$—H), 5.64(d,J=8Hz,—CH—),
             |

6.9–7.5 (m, arom. H), 8.92 (d, J=8 Hz, NH), 9.25 (d, J=9 Hz, NH)

SYNTHESIS EXAMPLE 21

Sodium 3-[D-2-[(2-oxoimidazolidin-1-yl)carboxamido]-2-thienylacetamido]-2-oxoazetidine-1-sulfonate $IR\nu_{max}^{KBr}cm^{-1}$: 3420, 3270, 1750, 1730, 1650, 1270, 1240, 1045.

NMR(DMSO-$d_6$, ppm): 3.17 (dd, J=2, 5 Hz, $C_4$—H), 3.10–3.47 (m, —$CH_2$—), 3.58 (t, J=5 Hz, $C_4$—H), 3.57–3.70 (m, —$CH_2$—), 4.83 (m, $C_3$—H), 5.63(d,J=8Hz,—CH—), 6.87–7.47 (m, arom. H), 7.54 (s, NH), 9.02 (d, J=8 Hz, NH), 9.25 (d, J=8 Hz, NH).

SYNTHESIS EXAMPLE 22

Sodium 3-[D-2-[(5-methoxycarbonyl-3-methyl-2-oxoimidazolidin-1-yl)carboxamido]-2-phenylacetamido]-2-oxoazetidine-1-sulfonate $IR\nu_{max}^{KBr}cm^{-1}$: 3480, 3260, 1750, 1728, 1662, 1260, 1048.

NMR(DMSO-$d_6$, ppm): 2.76 (s, $CH_3$), 3.10 (dd, J=3, 5 Hz, $C_4$—H), 3.70 (s, $CH_3$), 4.65(dd,J=4,10Hz,—CH—), 4.84(m,$C_3$—H), 5.38(d,J=8Hz,—CH—), 7.34 (s, arom. H), 9.12 (d, J=8 Hz, NH), 9.21 (d, J=8 Hz, NH).

SYNTHESIS EXAMPLE 23

Sodium 3-[D-2-[(5-benzyloxycarbonyl-3-methyl-2-oxoimidazolidin-1-yl)carboxamido]-2-phenylacetamido]-2-oxoazetidine-1-sulfonate $IR\nu_{max}^{KBr}cm^{-1}$: 3470, 3290, 1750, 1720, 1665, 1245, 1190, 1048.

NMR(DMSO-$d_6$, ppm): 2.76 (s, $CH_3$), 3.08 (dd, J=3, 5 Hz, $C_4$—H), 3.25 (dd, J=4, 10 Hz, —$CH_2$—), 3.56 (t, J=5 Hz, $C_4$—H), 3.70 (t, 10 Hz, —$CH_2$—), 4.71(dd,J=4,10Hz,—CH—), 4.80(m,$C_3$—H), 5.18(s,—$CH_2$—), 5.40(d,J=8Hz,—CH—), 7.36 (s, arom. H), 7.38 (s, arom. H), 9.12 (d, J=8 Hz, NH), 9.21 (d, J=8 Hz, NH).

An aqueous solution of the above compound is treated in a stream of hydrogen in the presence of palladium black to give sodium 3-[D-2-[(5-carboxy-3-methyl-2-oxoimidazolidin-1-yl)carboxamido]-2-phenylacetamido]-2-oxoazetidine-1-sulfonate.

$IR\nu_{max}^{KBr}cm^{-1}$: 3430, 3300, 1750, 1720, 1663, 1250, 1050.

NMR(DMSO-$d_6$, ppm): 2.75 (s, $CH_3$), 3.10 (dd, J=3, 5 Hz, $C_4$—H), 3.25–3.80 (m, $C_4$—H, —$CH_2$—), 4.48(m,—CH—), 5.38(d,J=8Hz,—CH—), 7.33 (s, arom. H), 9.12 (d, J=8 Hz, NH), 9.20 (d, J=8 Hz, NH).

SYNTHESIS EXAMPLE 24

Sodium 3-[2-(4-ethyl-2,3-dioxo-1-piperazinecarboxamido)-2-(2-chloro-1-cyclohexen-1-yl)acetamido]-2-oxoazetidine-1-sulfonate NMR(DMSO-$d_6$, ppm): 1.10 (t, J=7 Hz, $CH_3$), 1.60 (broad s, —$CH_2$—), 2.03 (broad s, —$CH_2$—), 2.33 (broad s, —$CH_2$—), 3.53 (m, —$CH_2$—), 3.90 (m, —$CH_2$—), 4.83 (m, $C_4$—H), 5.43(d,J=7Hz,—CH—), 8.66 (d, J=8 Hz, NH), 9.46 (d, J=7 Hz, NH)

SYNTHESIS EXAMPLE 25

Disodium 3-[2-(2-sulfonatoaminothiazol-4-yl)-2-[(1-tert-butoxycarbonyl-1-methylethoxy)imino]acetamido]-2-oxoazetidine-1-sulfonate $IR\nu_{max}^{KBr}cm^{-1}$: 1760, 1730, 1665, 1630, 1525, 1250, 1145, 1050.

NMR(DMSO-$d_6$, ppm): 1.39 (s, $CH_3$), 1.40 (s, $CH_3$), 3.35 (m, $C_4$—H), 4.95 (m, $C_3$—H), 6.83(s, ═〈H ), 9.10 (d, J=8 Hz, NH).

SYNTHESIS EXAMPLE 26

Sodium 3-[2-(2-tritylaminothiaozl-4-yl)-2-[(1-tert-butoxycarbonyl-1-methylethoxy)imino]acetamido]-2-oxoazetidine-1-sulfonate $IR\nu_{max}^{KBr}cm^{-1}$: 1760, 1730, 1675, 1590, 1570, 1280, 1260, 1200, 1140, 1040.

NMR(DMSO-$d_6$, ppm): 1.39 (s, $CH_3$), 1.40 (s, $CH_3$), 3.35 (m, $C_4$—H), 4.90 (m, $C_3$—H), 6.75(s, ═〈H ), 7.33 (s, arom. H), 9.03 (d, J=8 Hz, NH).

SYNTHESIS EXAMPLE 27

Sodium 3-[2-(2-chloroacetamidothiazol-4-yl)-2-(1-methylethoxyimino)acetamido]-2-oxoazetidine-1-sulfonae $IR\nu_{max}^{KBr}cm^{-1}$: 1755, 1700, 1540, 1250, 1050.

NMR(DMSO-$d_6$, ppm): 1.22 (d, J=6 Hz, $CH_3$), 3.66 (t, J=6 Hz, $C_4$—αH), 4.33 (s, —$CH_2$—),

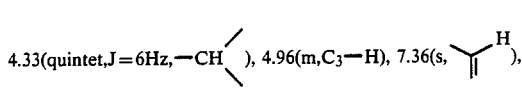

9.23 (d, J=8 Hz, NH).

SYNTHESIS EXAMPLE 28

Sodium 3-benzyloxycarboxamido-3-methoxy-2-oxoazetidine-1-sulfonate

IR$\nu_{max}^{KBr}$cm$^{-1}$: 1760, 1720, 1625, 1505, 1260, 1050.
NMR(DMSO-d$_6$, ppm): 3.36 (s, OCH$_3$), 3.56, 3.76 (each d, J=6 Hz, C$_4$—CH$_2$—), 5.13 (s, —CH$_2$—), 7.40 (s, arom. H), 8.90 (broad, s, NH).

SYNTHESIS EXAMPLE 29

Sodium 3-[2-(2-aminothiazol-4-yl)-2-(1-methylethoxyimino)acetamido]-2-oxoazetidine-1-sulfonate IR$\nu_{max}^{KBr}$cm$^{-1}$: 1760, 1660, 1620, 1525, 1250, 1050.
NMR(DMSO-d$_6$, ppm):

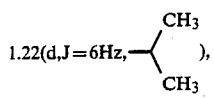

3.66 (t, J=6 Hz, C$_4$—αH), 4.33 (s, —CH$_2$—),

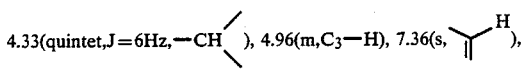

9.23 (d, J=8 Hz, NH).

SYNTHESIS EXAMPLE 30

Sodium 3-(2-oxo-2-phenylacetamido)-2-oxoazetidine-1-sulfonate

IR$\nu_{max}^{KBr}$cm$^{-1}$: 3375, 1760, 1668, 1510, 1272, 1238, 1180, 1050.
NMR(DMSO-d$_6$, ppm): 3.45 (dd, J=3, 6 Hz, C$_4$—H), 3.70 (t, J=6 Hz, C$_4$—H), 5.01 (ddd, J=3, 6, 9 Hz, C$_3$—H), 7.50–8.10 (m, arom. H), 9.65 (d, J=9 Hz, NH).

SYNTHESIS EXAMPLE 31

Sodium 3-[2-(2-mesylaminothiazol-4-yl)-2-(1-methylethoxyimino)acetamido]-2-oxoazetidine-1-sulfonate IR$\nu_{max}^{KBr}$cm$^{-1}$: 3450, 3275, 1760, 1660, 1532, 1470, 1240 1115, 1050.
NMR(DMSO-d$_6$, ppm):

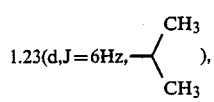

2.73 (s, CH$_3$), 3.33 (dd, J=3, 6 Hz, C$_4$—H), 3.63 (t, J=6 Hz, C$_4$—H),

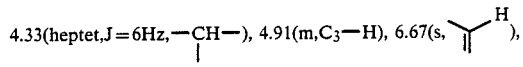

9.12 (d, J=9 Hz, NH).

SYNTHESIS EXAMPLE 32

Sodium 3-[2-(2-imino-3-mesyl-4-thiazolin-4-yl)-2-(1-methylethoxyimino)acetamido]-2-oxoazetidine-1-sulfonate IR$\nu_{max}^{KBr}$cm$^{-1}$: 3430, 3300, 1768, 1650, 1538, 1270, 1245, 1120, 1058, 1040.
NMR(DMSO-d$_6$, ppm):

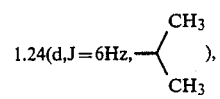

2.91 (s, CH$_3$), 3.30 (dd, J=3, 6 Hz, C$_4$—H), 3.65 (t, J=6 Hz, C$_4$—H),

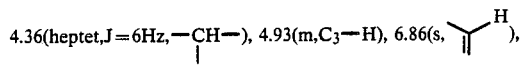

9.32 (d, J=9 Hz, NH).

SYNTHESIS EXAMPLE 33

Sodium 3-(2-bromo-2-phenylacetamido)-2-oxoazetidine-1-sulfonate

IR$\nu_{max}^{KBr}$cm$^{-1}$: 3325, 1760, 1670, 1533, 1240, 1055.
NMR(DMSO-d$_6$, ppm): 3.20 (m, C$_4$—H), 3.58 (t, J=5 Hz, C$_4$—H), 3.64 (t, J=6 Hz, C$_4$—H), 4.83 (m, C$_3$—H),

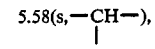

7.30–7.70 (m, arom. H), 9.28 (d, J=9 Hz, NH).

SYNTHESIS EXAMPLE 34

Sodium 3-(2-azido-2-phenylacetamido)-2-oxoazetidine-1-sulfonate

IR$\nu_{max}^{KBr}$cm$^{-1}$: 3460, 2110, 1755, 1670, 1240, 1053.
NMR(DMSO-d$_6$, ppm): 3.28, 3.35 (each dd, J=3, 6 Hz, C$_4$—H), 3.60, 3.63 (each t, J=6 Hz, C$_4$—H), 4.87 (m, C$_3$—H),

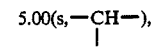

7.45 (s, arom. H), 9.17 (d, J=9 Hz, NH).

SYNTHESIS EXAMPLE 35

Sodium 3-tosylamino-2-oxoazetidine-1-sulfonate

IR$\nu_{max}^{KBr}$cm$^{-1}$: 3265, 3175, 1745, 1332, 1280, 1245, 1115, 1050.
NMR(DMSO-d$_6$, ppm): 2.42 (s, CH$_3$), 2.76 (dd, J=3, 6 Hz, C$_4$—H), 3.30 (t, J=6 Hz, C$_4$—H), 4.47 (dd, J=3, 6 Hz, $C_3$—H), 7.58 (ABq, J=9, 29 Hz, arom. H), 8.51 (broad s, NH).

SYNTHESIS EXAMPLE 36

Sodium 3-(2-phthalimido-2-thienylacetamido)-2-oxoazetidine-1-sulfonate

IR$\nu_{max}^{KBr}$cm$^{-1}$: 3345, 3070, 1753, 1710, 1520, 1380, 1240, 1195, 1100, 1045, 720.

SYNTHESIS EXAMPLE 37

Sodium 3-[2-azido-2-(3-chlorophenyl)acetamido]-2-oxoazetidine-1-sulfonate

IR$\nu_{max}^{KBr}$cm$^{-1}$: 3400, 2110, 1755, 1670, 1240, 1050.
NMR(DMSO-d$_6$, ppm): 3.31, 3.33 (each of dd, J=3, 6 Hz, $C_4$—H), 3.60, 3.63 (each t, J=6 Hz, $C_4$—H), 4.86 (m, $C_3$—H), 5.13(s,—CH—), 7.28–7.55 (m, arom. H), 9.15 (d, J=9 Hz, NH).

SYNTHESIS EXAMPLE 38

Sodium 3-(2-azido-2-phenylacetamido)-3-methoxy-2-oxoazetidine-1-sulfonate

IR$\nu_{max}^{KBr}$cm$^{-1}$: 3400, 2110, 1765, 1685, 1248, 1055.
NMR(DMSO-d$_6$, ppm): 3.13, 3.36 (each s, CH$_3$), 3.40–3.80 (m, $C_4$—H), 5.08(s,—CH—), 7.44 (s, arom. H), 9.63, 9.66 (each s, NH).

SYNTHESIS EXAMPLE 39

Sodium 3-[D-2-(4-cyclohexyl-2,3-dioxo-1-piperadinecarboxamido)-2-thienylacetamido]-2-oxoazetidine-1-suflonate IR$\nu_{max}^{KBr}$cm$^{-1}$: 3280, 1760, 1710, 1670, 1505, 1280–1230.
NMR(DMSO-d$_6$, ppm): 3.17 (dd, J=3, 6 Hz, $C_4$—$\beta$H), 3.61 (t, J=6 Hz, $C_4$—$\alpha$H), 4.85 (ddd, J=3, 6, 8 Hz, $C_3$—H), 5.70(d,J=7Hz,—CH—), 6.9–7.5 (m, arom. H), 9.29 (d, J=7 Hz, NH), 9.72 (d, J=7 Hz, NH).

SYNTHESIS EXAMPLE 40

Sodium 3-[2-(2-aminothiazol-4-yl)-2-(1-methylethoxyimino)actamido]-3-methoxy-2-oxoazetidine-1-sulfonate IR$\nu_{max}^{KBr}$cm$^{-1}$: 1770, 1670, 1620, 1530, 1245, 1055.
NMR(DMSO-d$_6$, ppm: 1.20, 1.22 (each d, J=6 Hz, CH$_3$), 3.41 (s, CH$_3$),

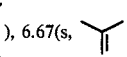

7.11 (broad s, NH$_2$), 9.72 (s, NH).

SYNTHESIS EXAMPLE 41

Sodium 3-[2-(2-mesylaminothiazol-4-yl)-2-(1-methylethoxyimino)acetamido]-3-methoxy-2-oxoazetidine-1-sulfonate IR$\nu_{max}^{KBr}$cm$^{-1}$: 3450, 3250, 1768, 1670, 1530, 1240, 1115, 1052.
NMR(DMSO-d$_6$, ppm): 1.22 (d, J=6 Hz, CH$_3$), 2.74 (s, CH$_3$),

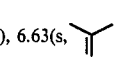

9.80 (s, NH).

SYNTHESIS EXAMPLE 42

Sodium 3-[D-2-(4-cyclohexyl-2,3-dioxo-1-pipeadinecarboxamido)-2-thienylacetamido]-3-methoxy-2-oxoazetidine-1-sulfonate IR$\nu_{max}^{KBr}$cm$^{-1}$: 2930, 1765, 1710, 1675, 1505, 1250, 1175, 1050.
NMR(DMSO-d$_6$, ppm): 3.16 (s, CH$_3$), 3.63 (ABq, J=6, 16 Hz, $C_4$—H), 5.89(d,J=7Hz,—CH—), 6.9–7.6 (m, arom. H), 9.71 (d, J=7 Hz, NH), 9.79 (s, NH).

SYNTHESIS EXAMPLE 43

Sodium 3-methoxy-3-[D-2-(4-piperidinecarbonylmethyl-2,3-dioxo-1-piperadinecarboxamido)-2-thienylacetamido]-2-oxoazetidine-1-sulfonate IR$\nu_{max}^{KBr}$cm$^{-1}$: 2930, 1765, 1705, 1680, 1635, 1505, 1250, 1050.
NMR(DMSO-d$_6$, ppm): 3.17 (s, CH$_3$), 3.57, 3.73 (ABq, J=6 Hz), 4.33 (s, —CH$_2$—), 5.90(d,J=7Hz,—CH—), 6.9–7.6 (m, arom. H), 9.70 (d, J=7 Hz, NH), 9.82 (s, NH).

SYNTHESIS EXAMPLE 44

Sodium 3-methoxy-3-[D-2-(4-phenyl-2,3-dioxo-1-piperadinecarboxamido)-2-thienylacetamido]-2-oxoazetidine-1-sulfonate IR$\nu_{max}^{KBr}$cm$^{-1}$: 3275, 1770, 1705, 1680, 1490, 1250, 1050.

NMR(DMSO-$d_6$, ppm): 3.19 (s, $CH_3$), 3.60, 3.74 (each d, J=6 Hz, $C_4$—H), 5.95(d, J=7Hz, —CH—),
|

6.9–7.6 (m, arom. H), 9.78 (d, J=7 Hz, NH), 9.84 (s, NH).

SYNTHESIS EXAMPLE 45

Sodium 3-[D-2-(4-t-butyl-2,3-dioxo-1-piperadinecarboxamido)-2-thienylacetamido]-3-methoxy-2-oxoazetidine-1-sulfonate IR$\nu_{max}^{KBr}$cm$^{-1}$: 3280, 2975, 1770, 1710, 1675, 1505, 1250, 1200, 1050.

NMR(DMSO-$d_6$, ppm): 1.40 (s, $CH_3$), 3.15 (s, $CH_3$), 3.55, 3.70 (each d, J=6 Hz, $C_4$—H), 5.88(d, J=7Hz, —CH—),
|

6.9–7.0 (m, arom. H), 9.65 (d, J=7 Hz, NH), 9.79 (s, NH).

SYNTHESIS EXAMPLE 46

Sodium 3-[D-2-[4-(3-methyl-2-butenyl)-2,3-dioxo-1-piperadinecarboxamido]-2-thienylacetamido]-3-methoxy-2-oxoazetidine-1-sulfonate IR$\nu_{max}^{KBr}$cm$^{-1}$: 3270, 1760, 1705, 1675, 1505, 1190.

NMR(DMSO-$d_6$, ppm): 1.70 (d, J=3 Hz, $CH_3$), 3.19 (s, $CH_3$), 3.43, 3.55 (each d, J=6 Hz, $C_4$—H), 5.88(d, J=7Hz, —CH—),
|

6.9–7.6 (m, arom. H), 8.35 (s, NH), 9.69 (s, NH), 9.73 (d, J=7 Hz, NH).

SYNTHESIS EXAMPLE 47

Sodium 3-[D-2-phenyl-2-[[3-(3-thienylidene)amino-2-oxoimidazolyldin-1-yl]carboxamido]acetamido]-2-oxoazetidine-1-sulfonate IR$\nu_{max}^{KBr}$cm$^{-1}$: 3290, 1755, 1720, 1660, 1525, 1270, 1225, 1050.

NMR(DMSO-$d_6$, ppm): 3.11 (dd, J=3, 6 Hz, $C_4$—$\beta$H), 3.57 (t, J=6 Hz, $C_4$—$\alpha$H), 3.80 (s, —$CH_2$—), 4.84 (dd, J=3, 6, 8 Hz, $C_3$—H), 5.43(d, J=8Hz, —CH—),
|

7.2–7.9 (m, arom. H), 7.89 (s, —CH=N—), 9.05 (d, J=8 Hz, NH), 9.21 (d, J=8 Hz, NH).

SYNTHESIS EXAMPLE 48

Sodium 3-[2-(4-hydroxyphenyl)-2-(4-methoxybenzyloxycarbonyl)acetamido]-3-methoxy-2-oxoazetidine-1-sulfonate IR$\nu_{max}^{KBr}$cm$^{-1}$: 1770, 1740, 1510, 1250, 1175, 1050.

NMR(DMSO-$d_6$, ppm): 3.10, 3.26 (each s, $CH_3$), 3.76 (s, $CH_3$), 4.79(s, —CH—),
|

5.06 (broad s, —$CH_2$—), 6.6–7.4 (m, arom. H), 9.36 (broad s, OH), 9.48 9.51 (each s, NH).

SYNTHESIS EXAMPLE 49

Disodium 3-[2-[(1-carboxy-1-methylethoxy)imino]-2-(2-tritylaminothiazol-4-yl)acetamido]-2-oxoazetidine-1-sulfonate IR$\nu_{max}^{KBr}$cm$^{-1}$: 3400, 1755, 1610, 1511, 1268, 1240, 1048.

NMR(DMSO-$d_6$, ppm): 1.36 (s, $CH_3$), 1.40 (s, $CH_3$), 3.36 (dd, J=3, 6 Hz, $C_4$—H), 3.49 (t, J=6 Hz, $C_4$—H), 4.70 (m, $C_3$—H),

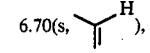

7.34 (s, arom. H), 8.59 (s, NH), 9.71 (d, J=8 Hz, NH).

EXAMPLE 1

Compound No. 3 (250 mg) is placed in a sterile 12-ml vial, which is then stoppered.

EXAMPLE 2

Compound No. 9 (500 mg) is placed in a 17-ml vial, which is then stoppered.

EXAMPLE 3

| | |
|---|---|
| Compound No. 12 | 125 mg |
| Lactose | 50 mg and |
| Magnesium oxide | 20 mg | are homogeneously mixed and made into a powder or fine granules. A capsule is packed with the powder or granules.

EXAMPLE 4

Cefotiam (250 g) is mixed with Compound No. 3 (44.3 g) under aseptic conditions, and the mixture is placed in sterile 12-ml vials in an amount of 250 mg (potency) per vial. The vials are then stoppered under vacuum (50 mmHg). On addition of 3 ml (per vial) of distilled water, the contents are easily dissolved.

EXAMPLE 5

Cefazoline (500 g) is mixed with Compound No. 9 (115.2 g) by proceeding as in Example 4, and the mixture is placed in 17-ml vials in an amount of 500 mg (potency) per vial. The vials are then stoppered.

EXAMPLE 6

Carbenicillin (250 g) and Compound No. 12 (70.2 g) are mixed under aseptic conditions, and the mixture is placed in sterilized and dried 17-ml vials in an amount of 250 mg (potency) per vial. The vials are then stoppered.

EXAMPLE 7

Ampicillin (250 g) and sterile and foreign-matter-free Compound No. 26 (35.2 g) are mixed under aseptic conditions, and the mixture is place in 9-ml vials in an amount of 125 mg (potency) per vial. The vials are then stoppered.

EXAMPLE 8

| | |
|---|---|
| Cephalexin | 125 mg |
| Compound No. 12 | 125 mg |
| Lactose | 50 mg and |
| Magnesium oxide | 10 mg | are homogeneously mixed and made into a powder. A capsule is packed with the powder.

EXAMPLE 9

Compound No. 33 (250 mg) is placed in a sterile 12-ml vial, which is then stoppered.

EXAMPLE 10

Compound No. 51 (500 mg) is placed in a 17-ml vial, which is then stoppered.

EXAMPLE 11

Cefotiam (250 g) and Compound No. 32 (35.5 g) are mixed under aseptic conditions, and the mixture is placed in sterile 12-ml vials in an amount of 250 mg (potency) per vial. The vials are then stoppered under vacuum (50 mmHg).

EXAMPLE 12

Ceftizoxime (100 g) and Compound No. 50 (200 g) are mixed under aseptic conditions, and the mixture is placed in sterile 17 ml vial in an amount of 250 mg (potency) per vial. The vials are then stoppered under vacuum.

EXAMPLE 13

Cefmenoxime (200 g) and Compound No. 53 (200 g) are mixtured under aseptic conditions, and the mixture is placed in sterile 28 ml vial in an amount of 500 mg (potency) per vial.

The vials are then stoppered under vacuum (30 mmHg).

EXAMPLE 14

Cefotaxime (250 g) and Compound No. 51 (125 g) are mixtured under aseptic conditions and the mixture is sterile 12 ml vial in an amount of 250 mg (potency) per vial.

The vials are then stoppered under vacuum (50 mmHg).

What is claimed is:

1. A β-lactamase inhibitory composition which comprises a β-lactamase inhibitory amount of a compound of the formula:

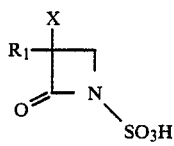

wherein $R_1$ is an amino group, a mono-acylated amino group the acyl group being derived from a carboxylic acid, or a protected amino group and X is hydrogen or methoxy, or a pharmaceutically acceptable salt thereof, and a cephalosporin.

2. A β-lactamase inhibitory composition as claimed in claim 1, wherein the cephalosporin is cephaloridine, cephalothin, cefazolin, cefalexin, cefacetril, cefamandolenafate, cefuroxime, cefotiam, cefoxitin, cefmetazole, cefsulodin, cefaclor, cefatrizine, cefotaxime, cefmenoxime, ceftazidine or ceftizoxime.

3. A β-lactamase inhibitory composition as claimed in claim 1, wherein X is hydrogen.

4. A β-lactamase inhibitory composition as claimed in claim 3, wherein $R^1$ is a group of the formula

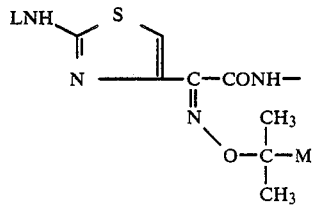

wherein L is sulfo, a lower alkylsulfonyl or trityl group and M is hydrogen or an esterified carboxyl group.

5. A β-lactamase inhibitory composition as claimed in claim 4, wherein $R_1$ is 2-[(1-t-butoxycarbonyl-1-methyl)ethoxyimino]-2-(2-sulfoaminothiazol-4-yl)acetamido.

6. A β-lactamase inhibitory composition as claimed in claim 4, wherein $R_1$ is 2-(2-mesylaminothiazol-4-yl)-2-(1-methylethoxyimino)acetamido.

7. A β-lactamase inhibitory composition as claimed in claim 3, wherein $R_1$ is a group of the formula:

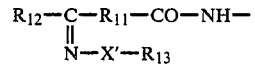

wherein X' is oxygen, $R_{12}$ is
 (a) a heterocyclic group which is unsubstituted or mono- to di-substituted by $C_{1-3}$ alkyl, $C_{1-3}$ alkoxy, hydroxyl, mesyl, halogen, imino, amino, mesylamino, $C_{2-4}$ acylamino or $C_{2-4}$ acylamino mono-substituted by halogen, or
 (b) phenyl which is unsubstituted or mono-substituted by (1) $C_{1-3}$ alkyl, (2) $C_{1-3}$ alkoxy, (3) halogen, (4) nitro, (5) amino, (6) hydroxyl, (7) benzyloxy, (8) benzoyloxy, (9) $C_{2-10}$ acyloxy, (10) γ-D-glutamyloxy or (11) 3-amino-3-carboxypropyloxy;

$R_{13}$ is
 (a) hydrogen,
 (b) phenyl which is unsubstituted or mono-substituted by $C_{1-3}$ alkyl, $C_{1-3}$ alkoxy or halogen,
 (c) lower acyl
 (d) lower acyl mono- to di-substituted by halogen,
 (e) lower alkyl,
 (f) a group of the formula $-R_{14}-R_{15}$ wherein $R_{14}$ is lower alkylene or lower alkenylene, and $R_{15}$ is carboxyl, esterified carboxyl or a heterocyclic group;

$R_{11}$ is a single bond or a group of the formula

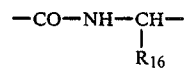

wherein
$R_{16}$ is
 (a) lower alkyl, (b) phenyl,
(c) phenyl mono-substituted by $C_{1-3}$ alkyl, $C_{1-3}$ alkoxy, halogen, nitro, amino or $C_{2-10}$ acyloxy, or
(d) a heterocyclic group which is unsubstituted or mono-substituted by (1) $C_{1-3}$ alkyl, (2) $C_{1-3}$ alkoxy, (3) halogen, (4) hydroxyl, (5) amino, (6) $C_{2-4}$ acylamino or (7) $C_{2-4}$ acylamino substituted by halogen.

8. A β-lactamase inhibitory composition as claimed in claim 1, wherein the compound of the formula is sodium 3-(2-azido-2-phenylacetamido)-2-oxoazetidine-1-sulfonate.

9. A β-lactamase inhibitory composition as claimed in claim 1, wherein
$R_1$ is
(A) a group of the formula

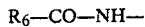

wherein
$R_6$ is
(i) lower alkyl
(ii) phenyl which is unsubstituted or mono-substituted by
 (1) $C_{1-3}$ alkyl, (2) $C_{1-3}$ alkoxy, (3) halogen, (4) nitro or (5) amino
(iii) a heterocyclic group
(iv) benzoyl
(B) a group of the formula:

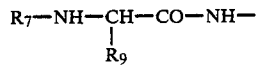

wherein $R_7$ is
(i) hydrogen,
(ii) an amino acid residue which is unsubstituted or mono- to di-substituted by amino, $C_{1-3}$ alkyl amino, amino protecting group, carbamoyl, methylcarbamoyl, sulfamoyl, benzyl, 4-ethyl-2,3-dioxo-1-piperazinecarbonyl or 4-ethyl-2,3-dioxo-1-piperazinecarbonylamino,
(iii) an amino-protecting group
(iv) a group of the formula $R_8$—$(CH_2)_{nl}$—CO— in which $R_8$ is
 (a) a heterocyclic group which is unsubstituted or mono- to tetra-substituted by (1) $C_{1-12}$ alkyl, (2) $C_{1-12}$ alkyl mono-substituted by phenyl, halogen, hydroxy or $C_{1-3}$ dialkylamino, (3) $C_{1-3}$ alkoxy, (4) hydroxy, (5) oxo, (6) thioxo, (7) formyl, (8) trifluoromethyl, (9) amino, (10) halogen, (11) $C_{1-3}$ alkylsulfonyl, (12) 2,6-dichlorophenyl (13) coumarin-3-carbonyl, (14) 4-formyl-1-piperazinyl, (15) pyrrolaldoimino, (16) furanaldoimino, (17) thiophenaldoimino, (18) mesyl, (19) amino-protecting group, (20) $C_{2-4}$ acylamino or $C_{2-4}$ acylamino mono-substituted by halogen
 (b) phenyl which is unsubstituted or mono-substituted by $C_{1-3}$ alkyl, $C_{1-3}$ alkoxy, halogen, hydroxy, or amino,
 (c) lower alkyl,
 (d) phenylthio which is unsubstituted or mono-substituted by $C_{1-3}$ alkyl, $C_{1-3}$ alkoxy, halogen, hydroxy or amino,
 (e) lower alkylthio, nl is 0 or an integer of 1 to 4; and the group —$(CH_2)_{nl}$— is unsubstituted or mono- to di-substituted by (1) amino or (2) a group of the formula —NH—$COR_8''''$ wherein $R_8''''$ is amino, piperazinyl or piperazinyl monosubstituted by $C_{1-3}$ alkyl, $C_{1-3}$ alkoxy, hydroxy, oxo, thioxo or halogen, (v) a group of the formula

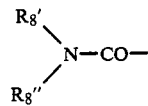

wherein $R_8'$ and $R_8''$ are independently (a) hydrogen, (b) lower alkyl, (c) lower alkyl-carbamoyl, (d) phenylcarbonyl or (e) phenylcarbonyl mono-substituted by $C_{1-3}$ alkyl, $C_{1-3}$ alkoxy, halogen, hydroxyl, hydroxysulfonyloxy or benzyloxy, (f) sulfo
(vi) a group of the formula $R_8'''$—$SO_2$— wherein $R_8'''$ is lower alkyl or lower alkyl mono- to di-substituted by amino, carboxyl, benzyloxycarbonyl or protected amino,
$R_9$ is
(i) hydrogen,
(ii) lower alkyl which is unsubstituted or mono-substituted by phenyl, carbamoyl, methylcarbamoyl, methylthio, thienylacetamide, ethoxycarbonylmethylcarbamoyl, N-methyltetrazolylthio, halogen or sulfamoyl,
(iii) phenyl which is unsubstituted or mono- to di-substituted by $C_{1-3}$ alkyl, $C_{1-3}$ alkoxy, halogen, hydroxy, hydroxysulfonyloxy, benzyloxy, benzoyloxy, trimethylsilyl or $C_{2-10}$ acyloxy,
(iv) a heterocyclic group which is unsubstituted or mono-substituted by (1) $C_{1-3}$ alkyl, (2) $C_{1-3}$ alkoxy, (3) halogen, (4) hydroxy, (5) nitro, (6) hydroxysulfonyloxy, (7) amino, (8) $C_{2-4}$acylamino or (9) $C_{2-4}$acylamino monosubstituted by halogen,
(v) cycloalkenyl
(vi) heterocycle-carbonylamino which is unsubstituted or mono- to tri-substituted by $C_{1-12}$ alkyl, $C_{1-3}$ alkoxy, oxo, thioxo or amino and which may have a $C_{1-3}$ alkylene chain between the heterocycle and carbonylamino moieties;
(C) a group of the formula:

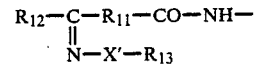

wherein
$X'$ is oxygen or sulfur,
$R_{12}$ is
(a) a heterocyclic group which is unsubstituted or mono- to di-substituted by $C_{1-3}$ alkyl, $C_{1-3}$ alkoxy, hydroxyl, mesyl, halogen, imino, amino, mesylamino, $C_{2-4}$ acylamino or $C_{2-4}$ acylamino mono-substituted by halogen, or
(b) phenyl which is unsubstituted or mono-substituted by (1) $C_{1-3}$ alkyl (2) $C_{1-3}$ alkoxy, (3) halogen, (4) nitro, (5) amino, (6) hydroxyl, (7) benzyloxy, (8) benzoyloxy, (9) $C_{2-10}$ acyloxy, (10) γ-D-glutamyloxy or (11) 3-amino-3-carboxypropyloxy;

$R_{13}$ is
  (a) hydrogen,
  (b) phenyl which is unsubstituted or mono-substituted by $C_{1-3}$ alkyl, $C_{1-3}$ alkoxy or halogen,
  (c) lower acyl,
  (d) lower acyl mono- to di-substituted by halogen,
  (e) lower alkyl,
  (f) a group of the formula $-R_{14}-R_{15}$ wherein $R_{14}$ is lower alkylene or lower alkenylene, and $R_{15}$ is carboxyl, esterified carboxyl or a heterocyclic group;

$R_{11}$ is a single bond or a group of the formula:

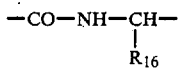

wherein $R_{16}$ is
  (a) lower alkyl,
  (b) phenyl,
  (c) phenyl mono-substituted by $C_{1-3}$ alkyl, $C_{1-3}$ alkoxy, halogen, nitro, amino or $C_{2-10}$ acyloxy, or
  (d) a heterocyclic group which is unsubstituted or mono-substituted by (1) $C_{1-3}$ alkyl, (2) $C_{1-3}$ alkoxy, (3) halogen, (4) hydroxyl, (5) amino, (6) $C_{2-4}$ acylamino or (7) $C_{2-4}$ acylamino substituted by halogen;

(D) a group of the formula

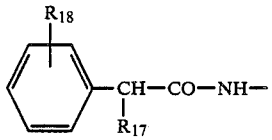

wherein
$R_{17}$ is
  (a) hydroxy,
  (b) hydroxysulfonyloxy,
  (c) carboxyl,
  (d) sulfamoyl,
  (e) sulfamoyl substituted by $C_{1-3}$ alkyl or amidino (f) sulfo,
  (g) phenoxycarbonyl,
  (h) phenoxycarbonyl mono-substituted by $C_{1-3}$ alkyl or $C_{1-3}$ alkoxy,
  (i) benzyloxycarbonyl,
  (j) formyloxy
  (k) phthalimido
  (l) azido or
  (m) halogen;

$R_{18}$ is
  (a) hydrogen,
  (b) lower alkyl,
  (c) lower alkoxy,
  (d) halogen,
  (e) azido,
  (f) nitro or
  (g) hydroxyl; and (E) a group of the formula:

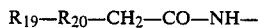

wherein
$R_{19}$ is
  (a) cyano,
  (b) phenyl,
  (c) phenyl mono-substituted by $C_{1-3}$ alkyl, $C_{1-3}$ alkoxy, halogen, nitro, amino, hydroxyl, aminomethyl or aminomethyl mono-substituted by carbamoyl, (2-oxo-3-benzylideneaminoimidazolidin-1-yl)carbonyl or (2-oxoimidazolidin-1-yl)carbonyl,
  (d) phenoxy,
  (e) phenoxy mono-substituted by $C_{1-3}$ alkyl, $C_{1-3}$ alkoxy, halogen, nitro, amino, hydroxy or aminomethyl,
  (f) $C_6$ alkyl,
  (g) lower alkyl mono- to tri-substituted by halogen, hydroxyl, cyano or trifluoromethyl,
  (h) a heterocyclic group which is unsubstituted or mono- to tri-substituted by $C_{1-3}$ alkyl, $C_{1-3}$ alkoxy, halogen, nitro, hydroxyl, amino, amino-protective group, carboxyl, oxo, $C_{2-4}$ acylamino, $C_{2-4}$ acylamino mono-substituted by halogen, or $C_{2-4}$ acyl; and $R_{20}$ is a single bond or $-S-$.

* * * * *